(12) United States Patent
Sugita et al.

(10) Patent No.: US 6,767,735 B1
(45) Date of Patent: Jul. 27, 2004

(54) VECTOR FOR INTRODUCING A GENE INTO A PLANT USING A SELECTABLE MARKER

(75) Inventors: Koichi Sugita, Tokyo (JP); Hiroyasu Ebinuma, Tokyo (JP); Mika Kaneda, Tokyo (JP)

(73) Assignee: Nippon Paper Industries Co., Ltd., Tokyo (JP)

( * ) Notice: Subject to any disclaimer, the term of this patent is extended or adjusted under 35 U.S.C. 154(b) by 0 days.

(21) Appl. No.: 09/477,730

(22) Filed: Jan. 5, 2000

(30) Foreign Application Priority Data

Jan. 6, 1999 (JP) .......................................... P. 11-000828
Dec. 2, 1999 (JP) .......................................... P. 11-343937

(51) Int. Cl.$^7$ ............................................. C12N 15/82
(52) U.S. Cl. .................................... 435/320.1; 800/290
(58) Field of Search ............................ 435/320.1, 419, 435/468; 800/290, 278, 298

(56) References Cited

U.S. PATENT DOCUMENTS 5,965,791 A * 10/1999 Ebinuma et al. ............ 800/205

FOREIGN PATENT DOCUMENTS

| EP | 0 716 147 | 6/1996 |
|---|---|---|
| WO | WO 99/38988 | 8/1999 |

OTHER PUBLICATIONS

Walden et al, Techniques in plant molecular biology–progress and problems, 1990, Eur. J. Biochem. vol. 192 pp. 563–576.*

Davies. Plant hormones and their role in plant growth and development. 1987, Martinus Nijhoff Publishers, pp. 4–9.*

Hedden et al. Manipulation of hormone biosynthetic genes in transgenic plants. Current Opinion in Biotechnology, 2000, vol. 1 pp. 130–137.*

McCourt. Genetic analysis of hormone signaling. Ann. Rev. Plant Physiol. Plant Mol. Biol. 1999, vol. 50, pp. 219–243.*

T. Kakimoto, Science, vol. 274, No. 274, pp. 982 to 895, "CKI1, A Histidine Kinase Homolog Implicated in Cytokinin Signal Transduction", Nov. 8, 1996.

O. Nilsson, et al., Physiologia Plantarum, vol. 100, No. 3, pp. 463 to 473, "Getting to the Root: The Role of the Agrobacterium Rhizogenes Rol Genes in the Formnation of Hairy Roots", 1997.

H. Ebinuma, et al., Proc. Natl. Acad. Sci., vol. 94, No. 94, pp. 2117 to 2121, "Selection of Marker–Free Transgenic Plants Using the Isopentenyl Transferase Gene", Mar. 1997.

J. Shah, et al., Molecular Plant–Microbe Interactions, vol. 10, No. 1, pp. 69 to 78, "Characterization of a Salicylic Acid–Insensitive Mutant (sai1) of Arabidopsis Thaliana, Identified in a Selective Screen Utilizing the SA–Inducible Expression of the tms2 Gene", 1997.

L. J. Klimczak, et al., Plant Physiology, vol. 109, No. 2, pp. 687 to 696, "Multiple Isoforms of Arabidopsis Casein Kinase I Combine Conserved Catalytic Domains With Variable Carboxyl–Terminal Extensions", 1995.

* cited by examiner

Primary Examiner—David T. Fox
Assistant Examiner—Cynthia Collins
(74) Attorney, Agent, or Firm—Oblon, Spivak, McClelland, Maier & Neustadt, P.C.

(57) ABSTRACT

A vector for introducing a gene into a plant, wich comprises a desired gene, and a plant hormone signal transduction gene as a selectable marker gene.

4 Claims, 18 Drawing Sheets pIPTPCKI-4 (17.8 kb)

VECTOR FOR INTRODUCING A GENE INTO A PLANT USING A SELECTABLE MARKER

BACKGROUND OF THE INVENTION

1. Field of the Invention

The present invention relates to a novel useful vector for introducing a gene into a plant using genetic engineering techniques.

2. Description of the Background

Transformation of microorganisms and cultured cells using genetic engineering is currently applied to the production of physiologically active substances useful as medicines and the like, and thus greatly contributes to the industry. In the field of plant breeding, since this technology enables a desired gene to be directly introduced into plants to be bred, it has the following advantages compared to classical breeding which requires multiple crossing: (a) it is possible to introduce only a characteristic to be improved; (b) it is possible to introduce characteristics of species other than plants (such microorganisms and the like); and (c) it is possible to greatly shorten the breeding period. Industrial application of plant genetic engineering lags behind because, for example, the life cycles of plants are much longer than those of microorganisms and the like and it has been difficult to introduce a gene into plants. However, a number of useful transgenic plants have been produced mainly in Europe and the U.S. and are now on the market.

Specifically, the production of a transgenic plant by introducing a desired gene into a plant requires the following three steps: (1) introducing the desired gene into the plant cell (including introduction of the same into the chromosomes, nucleus and the like); (2) selecting plant tissue made only of cells into which the desired gene has been introduced; and (3) regenerating a plant from the selected plant tissue. Among these steps, in selecting the desired transgenic tissue, generally, since it is difficult to confirm with the naked eye a tissue in which the desired gene is expressed (the tissue in which the desired gene is expressed is naturally a tissue constituted by cells into which the gene is introduced) without regenerating a plant, the desired gene is introduced into a plant cell together with a selectable marker gene of which expression can be easily detected at the stage of cell culturing, and the presence or absence of the expression of the selectable marker gene (namely, the presence or absence of the introduction of the selectable marker gene) is used as an index for the introduction of the desired gene. Examples of the selectable marker gene include a kanamycin-resistant gene (NPTII: neomycin phosphotransferase gene) and a hygromycin-resistant gene (hygromycin phosphotransferase gene) which impart resistance to antibiotics, a nopaline synthetase gene (NOS) and an octopine synthetase gene (OCS) which relate to amino acid synthesis, and a sulfonylurea-resistant gene (ALS: acetolactate synthetase gene) which imparts resistance to agricultural chemicals.

However, the expression of a selectable marker gene can cause serious problems when such a transgenic plant is used for food. Namely, it is quite difficult to ensure safety of the gene product obtained by the expression of the selectable marker gene on the human body. Consequently, when a transgenic plant produced using a selectable marker gene as an index is sold as food, it is necessary to carry out detailed examination on the effect of the gene product upon the human body. For example, although the NPTII gene has been already often used as a selectable marker gene at a laboratory level since the early 1980's, its gene product was approved by Food and Drug Administration (FDA) as a food additive for the first time in 1994, and transgenic plants to which the gene is introduced as a selectable marker gene have been used for food thereafter. However, uneasiness about such NPTII gene products is still present unavoidably at the essential level of consumers who actually eat these products.

Also, all of the genes which have so far been put into practical use as selectable marker genes, including the NPTII gene, are genes that contribute to the detoxication activity of plant cell growth inhibitors, so that selection of a tissue introduced with a desired gene is carried out by culturing the tissue using a medium containing such a growth inhibitor and evaluating the presence or absence of the expression of the selectable marker gene, namely resistance to the inhibitor, as an index. In that case, however, the presence of resistance, namely the ability of the plant tissue to grow in the presence of such an inhibitor, is merely a matter of degree, so that it is difficult to avoid undesirable influences of the culturing in the presence of such an inhibitor upon plant cells, and such influences are actually causing side effects, such as reduction of proliferation and redifferentiation ratio of the transgenic tissue due to decreased activity of the plant cells.

Furthermore, after selection of a transgenic tissue, expression of a selectable marker gene causes considerable obstacles even at the level of researchers studying the plant breeding. That is, when a transgenic plant which has been produced by using a selectable marker gene is again introduced by another gene, introduction of the gene cannot be carried out using the same selectable marker gene. In other words, since the selectable marker gene has been already present in the plant, the selectable marker gene is always expressed in the plant whether or not the new desired gene is introduced into the plant together with the selectable marker gene. Therefore, such a selectable marker gene can no longer be used as an index of the introduction of the new desired gene. Consequently, the number of times of repeated gene introduction into a certain plant is naturally restricted by the number of different selectable marker genes useful in the plant. However, kinds of selectable marker genes so far available are not so many. Additionally, all of the selectable marker genes are not necessarily useful in the plant of the object.

As a means for resolving these problems, the inventors of the present invention have previously provided a novel vector in International Publication No. WO 96/15252 and U.S. Pat. No. 5,965,791. This vector uses a morphological abnormality induction gene as a selectable marker gene which is present in plants in the natural world and whose safety upon the human body is secured to a certain degree. Additionally, when introduction of a gene into a plant is carried out using this vector, a transgenic tissue can be selected easily using its morphology as an index. That is, a tissue after a gene introduction treatment is cultured under appropriate conditions, and a tissue formed during the culturing showing morphological abnormality is detected and selected. It is not necessary to add an inhibitor which reduces plant cell activity to the medium during the culturing. Also, when introduction of a gene into a plant is carried out using this vector in which the selectable marker gene is used in combination with a removable DNA element, a transgenic tissue from which influences of the selectable marker gene are completely removed can be obtained. Such a tissue can be obtained easily by merely carrying out its selection using morphology of the transgenic tissue as an index similar to the case of the above-described gene introduction.

However, such a vector also has a problem that the selection efficiency of transgenic tissues is poor. That is, even when tissues after the gene introduction treatment are cultured and a tissue having morphological abnormality is selected in the above-described manner, the thus selected tissue is often not the transgenic tissue. This result suggests that a plant hormone or the like produced in the cell to which the morphological abnormality induction gene has been introduced is also moved into its peripheral cells and exerts influences thereon, and that tissues having morphological abnormality are differentiated and proliferated from the influenced non-transgenic cells.

SUMMARY OF THE INVENTION

An object of the present invention is to improve selection efficiency of transgenic tissues and solving the above-described problems involved in the previous techniques in the introduction of a gene into plants.

As a result of intensive studies, the inventors of the present invention have found that the above-described problems can be solved by the use of a plant hormone signal transduction gene as a selectable marker gene, and thus the present invention has been completed.

That is, the present invention relates to a vector for introducing a gene into a plant, which comprises a desired gene, and a plant hormone signal transduction gene as a selectable marker gene.

DETAILED DESCRIPTION OF THE INVENTION

Figure 1:
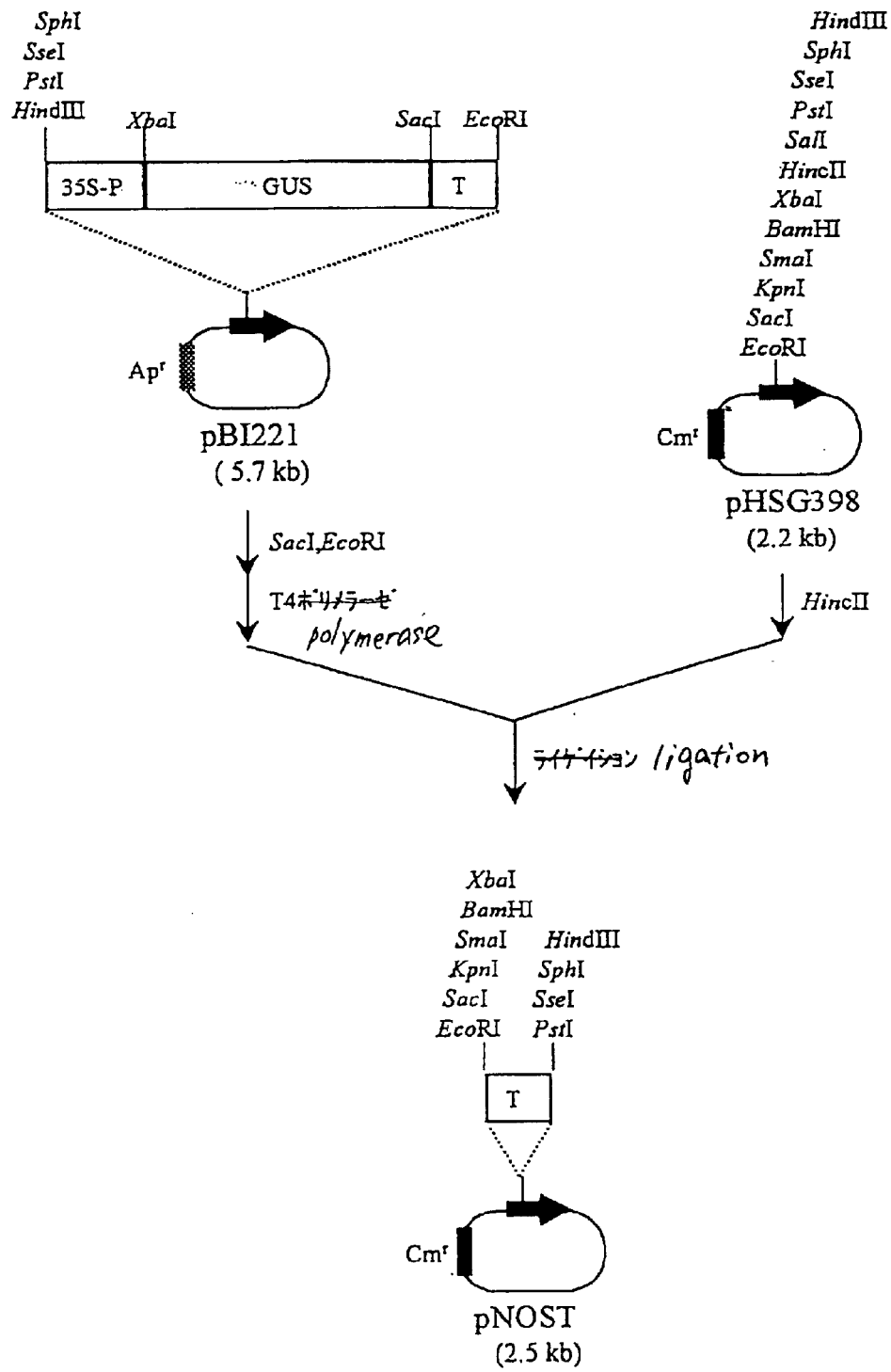
FIG. 1 is a diagram of the construction of pNOST in the pIPTPCKI-4 construction scheme.
Figure 2:
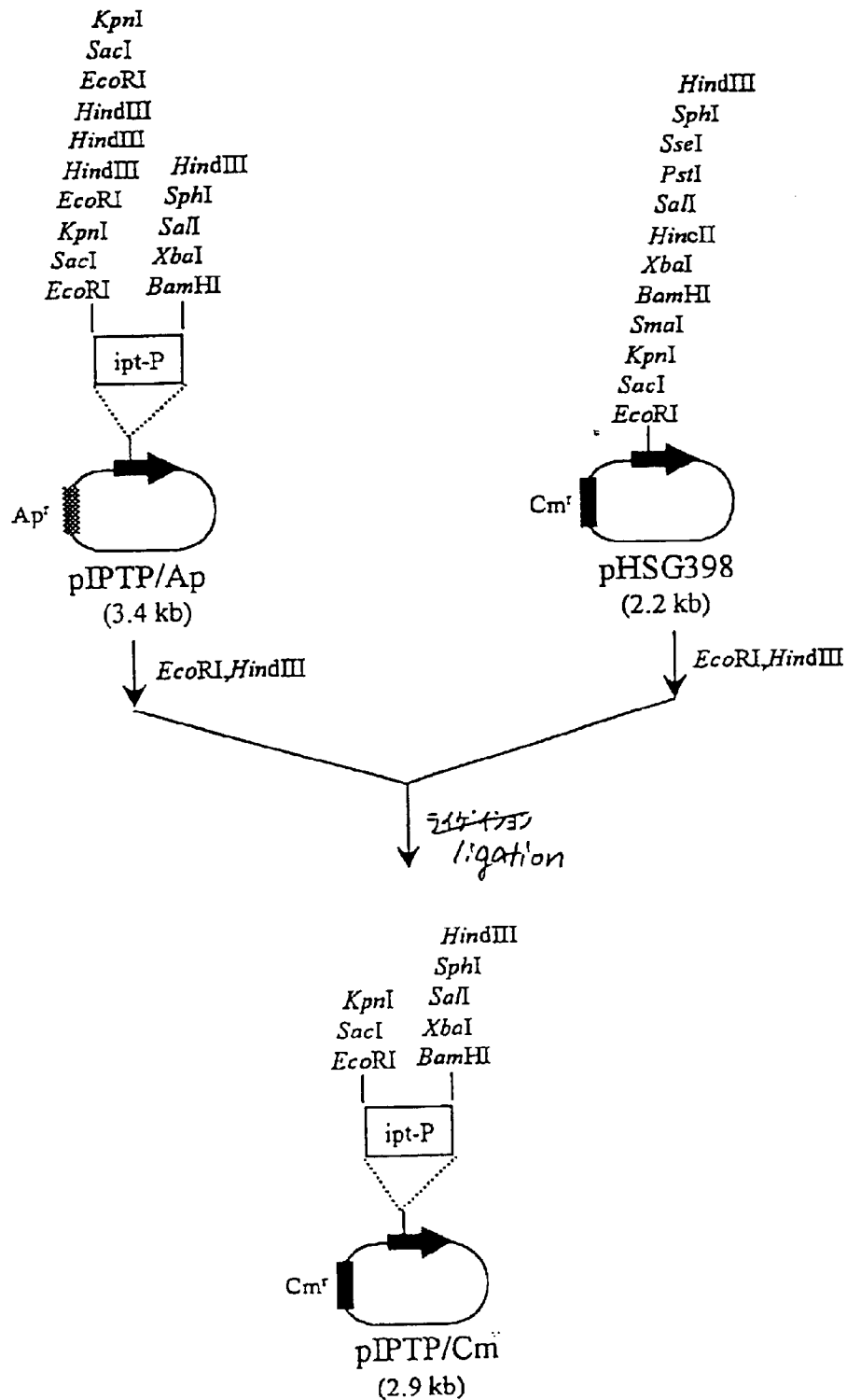
FIG. 2 is a diagram of the construction of pIPTP/Cm from pIPTP/Ap in the pIPTPCKI-4 construction scheme.
Figure 3:
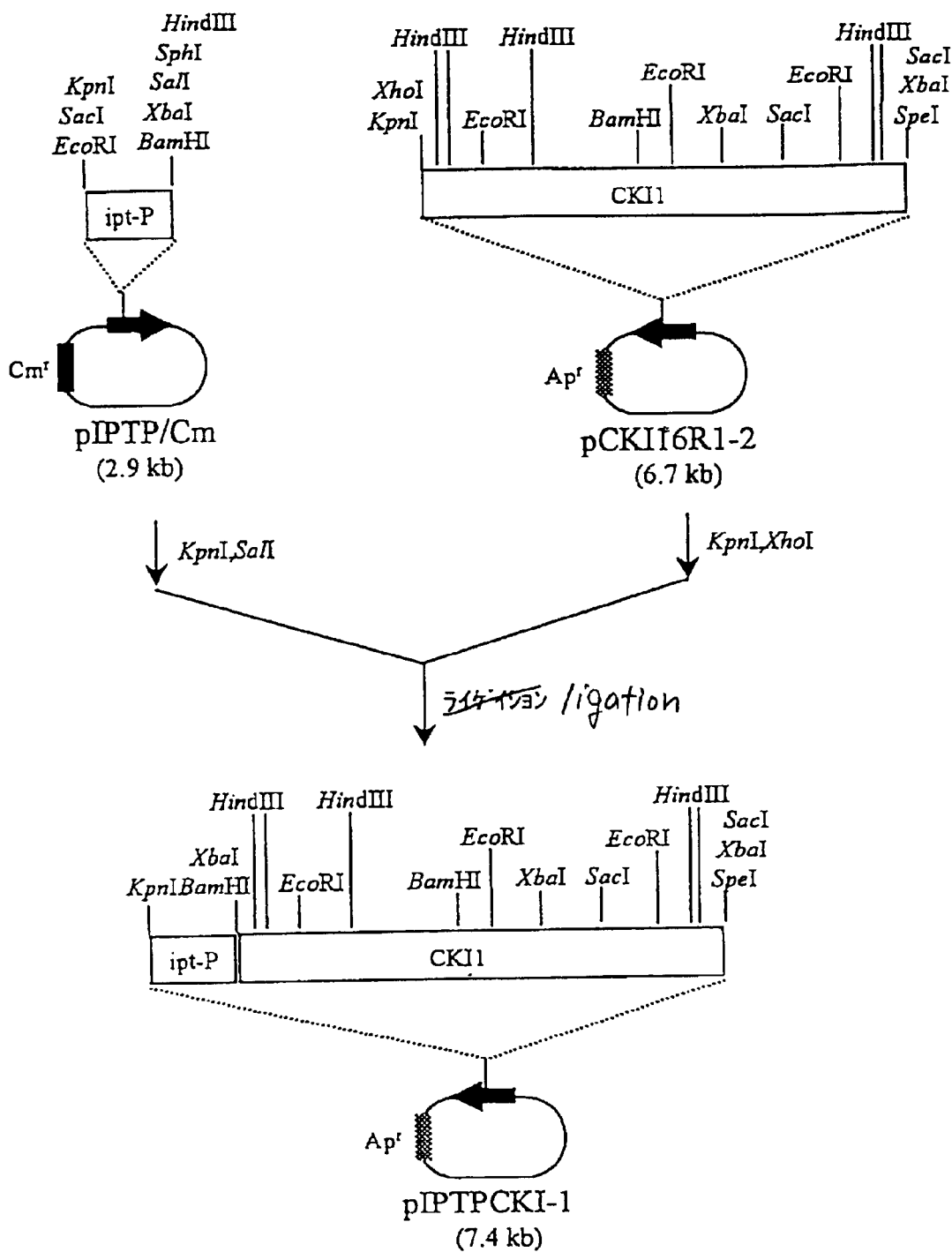
FIG. 3 is a diagram of the construction of pIPTPCKI-1 from pIPTP/Cm in the pIPTPCKI-4 construction scheme.
Figure 4:
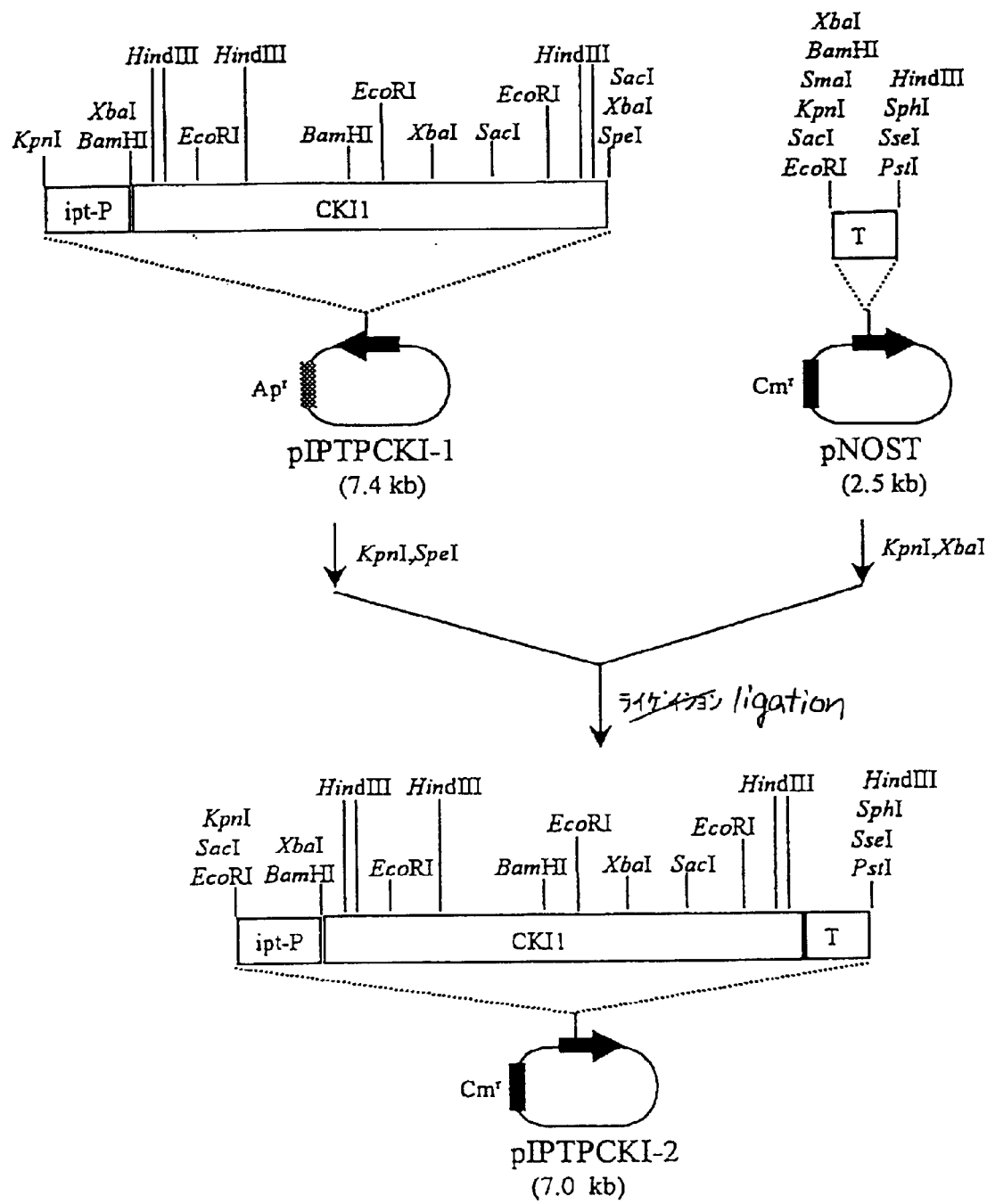
FIG. 4 is a diagram of the construction of pIPTPCKI-2 from pIPTPCKI-1 in the pIPTPCKI-4 construction scheme.
Figure 5:
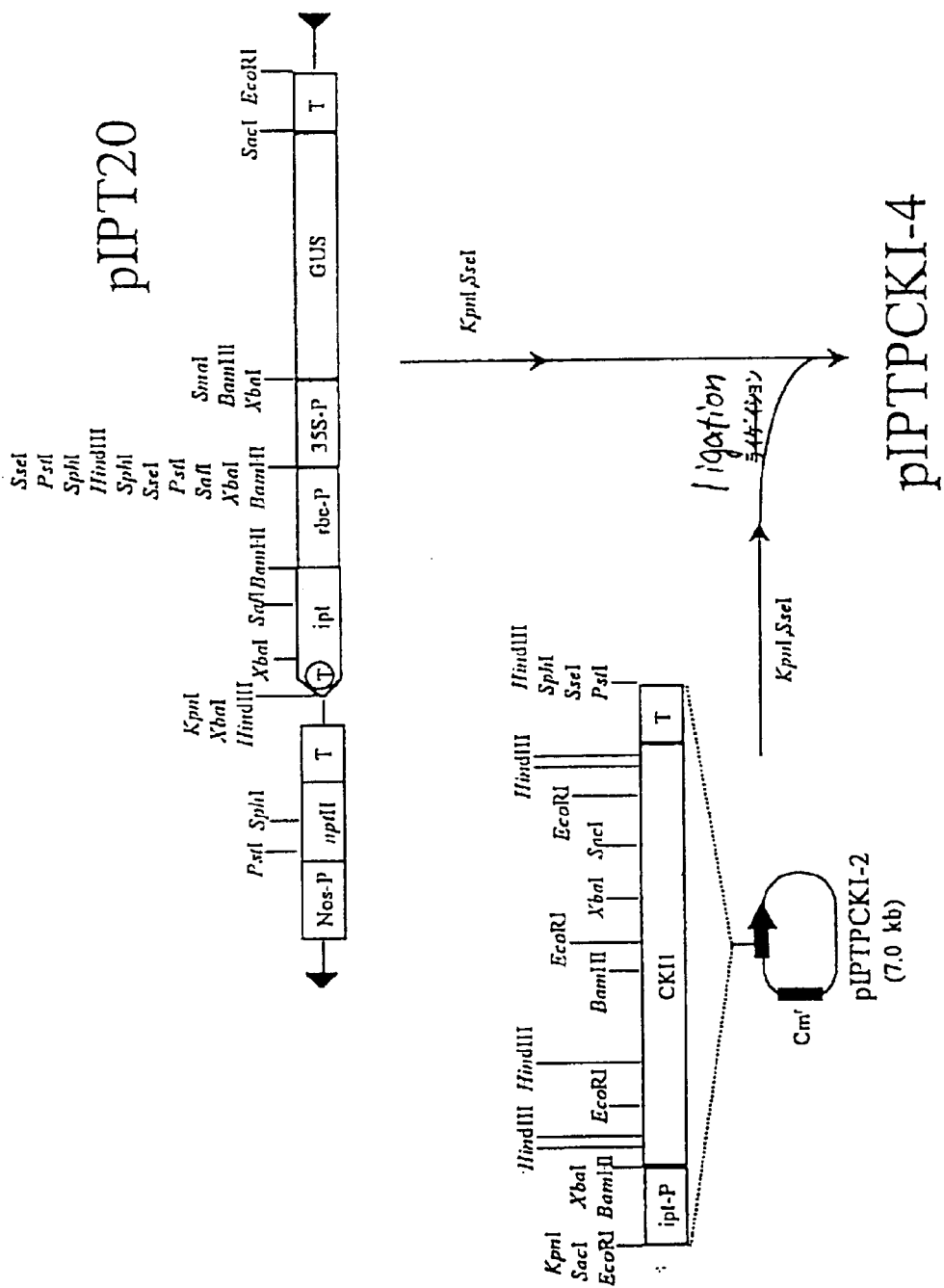
FIG. 5 is a diagram of the construction of pIPTPCKI-4 from pIPTPCKI-2 in the pIPTPCKI-4 construction scheme.

The present invention will be described below in detail.

The term "plant hormone signal transduction gene" as used herein means any one of genes encoding sensors that recognize the presence of a plant hormone, such as gibberellin, ethylene, auxin, cytokinin or the like, and proteins related to a series of signal transduction pathways in which the information is transferred from the sensors. Examples of the plant hormone signal transduction gene include ETR1 gene which is an ethylene receptor gene (C. Chang et al., *Science*, 262: 539 (1993)), CKI1 gene (K. Kakimoto, *Science*, 274: 982 (1996)) and mutants thereof (e.g., CKI2 gene) and GCR1 gene (S. Plakidou-Dymock et al., *Current Biology*, 8: 315 (1998)) which are considered to be a cytokinin receptor gene, IBC6 gene and IBC7 gene (I. Brandstatter and J. J. Kieber, *The Plant Cell*, 10: 1009 (1998)), as reported in C. Chang and R. C. Stewart, *Plant Physiol.*, 117: 723 (1998).

Among these plant hormone signal transduction genes, the CKI1 gene has been studied most in detail and is useful as the plant hormone signal transduction gene of the present invention, because it improves sensitivity for cytokinin in plant cells into which the gene has been introduced and, as a result, induces differentiation of a multiple bud tissue which has a characteristic morphology, can be detected easily with the naked eye and grows actively. As a matter of course, any gene which does not induce morphological abnormality, unlike the case of the CKI1 gene, can also be used in the present invention, so long as it belongs to a plant hormone signal transduction gene. Since the sensitivity for a plant hormone changes in plant cells into which such a gene has been introduced, a plant cell which, for example, does not grow in a plant hormone-free medium by nature shows active growth by the influence of a plant hormone (endogenous plant hormone) inherently produced by the cell per se. Consequently, a transgenic tissue can be selected using the difference in such behavior against a plant hormone as an index.

Also, according to the present invention, a plant hormone synthesis gene may be used together with the plant hormone signal transduction gene as selectable marker genes. The term "plant hormone synthesis gene" as used herein means a gene related to the synthesis of a plant hormone, such as gibberellin, ethylene, auxin, cytokinin, or the like. Examples of the auxin synthesis gene include iaaM (tryptophan monooxygenase) gene (H. Van Onckelen et al., *FEBS Lett.*, 198: 357 (1986)) and iaaH (indolacetamide-hydrolase) gene (L. S. Thomashow, *Proc. Natl. Acad. Sci. USA*, 81: 5071 (1984)) both produced by bacteria belonging to the genus Agrobacterium, and an aldehyde oxidase gene (JP-A-10-10-8680; the term "JP-A" as used herein means an "unexamined published Japanese patent application") and a nitrilase gene (D. Bartling et al., *Eur. J. Biochem.*, 205: 417 (1992)) in plants. Furthermore, examples of the cytokini synthesis gene include ipt (isopentenyl transferase) gene which is present on the T-DNA of *Agrobacterium tumefaciens* (hereinafter referred to as "*A. tumefaciens*") (D. Akiyoshi, *Proc. Natl. Acad. Sci. USA*, 81: 5994 (1984)) and APRT (adenine phosphoribosyltransferase) gene (K. M. Schnorr, *Plant J.*, 9: 891 (1996)) in plants. Moreover, gibberellin and ethylene synthesis genes from various plants have been isolated (*Cell Engineering Supplement, Plant Cell Engineering Series* 10, "Signal Transduction of Plant Hormones— From Biosynthesis to Physiological Functions", pp. 86–96 and pp. 138–150). Any one of these genes can be used in the present invention. However, among these, the ipt gene is suitable as the plant hormone synthesis gene of the present invention because it can be introduced into various plants and its ability to function in these plants can be revealed.

According to the present invention, the selectable marker gene may be used in combination with a removable DNA element. In this case, a vector is constructed by inserting the selectable marker gene of the present invention into such a position that it behaves integrally with the removable DNA element and by inserting the desired gene into such a position that it does not behave integrally with the removable DNA element. A transgenic tissue from which the influence of the selectable marker gene has been completely removed can be obtained easily by introducing a gene into a plant using the thus constructed vector.

The term "removable DNA element" as used herein means an element of a DNA sequence which itself is removable from the DNA wherein the DNA element exists and functions. In plants, a transposon present in a chromosome is known as this element. The structure, activity and behavior of transposons have been almost completely identified. For the transposon to function, two components are required in principle, an enzyme which is expressed from the gene present therein and which catalyzes the excision and transposition of the transposon itself (transposase), and a DNA binding sequence which is present in the terminal region of the transposon and upon which the transposase acts. By these elements, the transposon is excised from the chromosome in which it exists, and is then usually transposed to a new position in the DNA. However, at a certain ratio, the transposon also disappears without being transposed. The present invention makes use of such a transposition error of the transposon. The transposon can be one of two types, either an autonomous transposon or a non-autonomous transposon. The autonomous transposon maintains the two elements, the transposase and the DNA binding sequence. In the autonomous transposon, the transposase is expressed and binds to the DNA binding sequence for action, whereby the transposon is autonomously excised from the chromosome. The non-autonomous transposon retains the terminal DNA binding sequence to which the transposase is bound for action. In the non-autonomous transposon, the transposase gene undergoes mutation such that the transposase is not expressed; thus the transposon cannot be excised from the chromosome autonomously. However, when transposase is supplied to the non-autonomous transposon from the autonomous transposon or from an independent transposase gene, the non-autonomous transposon behaves similarly to the autonomous transposon.

Examples of the autonomous transposons include Ac and Spm isolated from maize (A. Gierl and H. Saedler, *Plant Mol. Biol.*, 19: 39 (1992)). Ac can be obtained by digesting wx-m7 locus in the chromosome of the maize with restriction endonuclease Sau3A (U. Behrens et al., *Mol. Gen. Genet.*, 194: 346 (1984)). This autonomous transposon is the most analyzed among plant transposons. In fact, the DNA sequence has already been determined (M. Mueller-Neumann et al., *Mol. Gen. Genet.*, 198: 19 (1984)), and it is suitable for the DNA element used in the present invention. Also, examples of non-autonomous transposons include Ds and dspm obtained by deleting the inner regions of Ac and Spm, respectively (H.-P. Döring and P. Starlinger, *Ann. Rev. Genet.*, 20: 175 (1986)) and those isolated from many plants, other than maize, such as snapdragon, morning glory and the like (for example, Y. Inagaki et al., *Plant Cell*, 6: 375 (1994)). When these transposons are introduced into chromosomes of exogenous plants, these transposons are also excised from a chromosome and transposed (for example, B. Baker et al., *Proc. Natl. Acad. Sci. USA*, 83: 4844 (1986).

In the present invention, both the autonomous and non-autonomous transposons can be used. For example, a non-autonomous transposon can be used by inserting therein a selectable marker gene and a transposase gene which is obtained from an autonomous transposon or synthesized.

Another removable DNA element, which is not present in plants, is an element derived from a site-specific recombination system. The site-specific recombination system consists of two elements, a recombination site (corresponding to the removable DNA element of the present invention) having a characteristic DNA sequence, and an enzyme (recombinase) that binds to the DNA sequence specifically and catalyzes the recombination between these DNA sequences if two or more of the sequences exist. When the two DNA sequences are oriented in the same direction at a given interval on the same DNA molecule, the region held by these DNA sequences is excised from the DNA molecule, such as a plasmid, chromosome or the like. When the two DNA sequences are oriented in opposite directions on the same DNA molecule, the region held by these DNA sequences is inverted. The present invention utilizes the former excision. Both excision and inversion within the recombination site occur as a result of homologous recombination through the site-specific recombination system, which is different from the mechanism using the transposon in which its excision occurs as a step of transposition. The recombinase gene is not necessarily present in the same DNA molecule, in which the recombination site exists. The recombinase gene only needs to be present in the same cell and expressed to excise or invert the region held by the two DNA sequences (N. L. Craig, *Annu. Rev. Genet.*, 22: 77 (198)).

At present, site-specific recombination systems have been identified in microorganisms such as phage, bacterium (e.g., *E. coli*), yeast and the like. Although examples thereof include a Cre/lox system, an R/RS system, a FLP system, a cer system, and a firm system (for example, N. L. Craig, *Annu. Rev. Genet.*, 22: 77 (1988)), they have not been found in higher organisms. However, when the site-specific recombination system separated from these microorganisms is introduced into organisms (including plants) different from the organism from which this system has been derived, it behaves in the same way as in the original organism. In the examples of the present application, the R/RS system (H. Matsuzaki et al., *J. Bacteriology*, 172: 610 (1990)), the site-specific recombination system of yeast (*Zygosaccharomyces rouxii*), was used by inserting a recombinase gene into its recombination site. This R/RS system also maintains its inherent function in higher plants (H. Onouchi et al., *Nucleic Acid Res.*, 19: 6373 (1991)).

Furthermore, in the present invention, when the selectable marker gene is used in combination with a removable DNA element, it can be inserted into a position where it is removed together with the removable DNA element. For example, when a transposon is used as the removable DNA element, the selectable marker gene can be inserted into a position which has no influence on removing of the transposon, namely a position between upstream of the introduction gene promoter region and downstream of the terminal region to which the transferase is linked. Also, when the R/RS system is used, the selectable marker gene can be inserted into any position, so long as it does not inhibit expression of the recombinase within the region of the recombination site.

The vector of the present invention can be used in any plants into which the gene can be introduced by genetic engineering methods. The desired gene in accordance with the present invention can be any gene by which agriculturally excellent characteristics can be imparted and any gene which allows for studies of gene expression mechanisms and the like, though agriculturally excellent characteristics are not necessarily imparted.

Also, when a protein, such as an enzyme or the like, is produced from a gene, the gene generally requires not only the structural gene encoding the information on such a polypeptide but also regulator sequences, such as a promoter (expression initiation sequence), a terminator (expression termination sequence), and the like. When the term "gene" is simply used, it generally means a structural gene having these regulator sequences. In the present invention, such promoters and terminators can be used without limitation, so long as they can function in the objective plant. Examples of the useful promoters include a cauliflower mosaic virus 35S promoter (J. T. Odell et al., Nature (London), 313: 810 (1985)), the promoter of a nopaline synthetase (W. H. R. Langridge et al., Plant Cell Rep., 4: 355 (1985)), and various induction promoters, for example, chemical substance induction promoters, such as a glutathione-S-transferase I system gene promoter (JP-A-5-268965), a glutathione-S-transferase II system (GST-II) gene promoter (International Patent Publication WO 93/01294), a Tet repressor fusion cauliflower mosaic virus 35S promoter (C. Gatz et al., Mol. Gen. Genet., 227: 229 (1991)), a Lac operator/repressor system promoter (R. J. Wilde et al., EMBO J., 11: 1251, 1992), an alcR/alcA system promoter (International Patent Publication WO 94/03619), a glucocorticoid system promoter (T. Aoyama, Protein, Nucleic Acid and Enzyme, 41: 2559 (1996)), a par system promoter (T. Sakai et al., Plant Cell Physiol., 37: 906 (1996)), and the like; heat induction promoters, such as an hsp80 promoter (JP-A-5-276951) and the like; and light induction promoters, such as a ribrose-bisphosphate carboxylase small subunit (rbcS) gene promoter (R. Fluhr et al., Proc. Natl. Acad. Sci. USA, 83: 2358 (1986)), a fructose-1,6-bisphosphatase gene promoter (JP-W-7-501921; the term "JP-W" as used herein means an "unexamined published Japanese international patent application"), a light-harvesting chlorophyll a/b binding protein gene promoter (JP-A-5-89), and the like. Examples of the useful terminator sequences include a nopaline synthetase polyadenylation signal (A. Depicker et al., J. Mol. Appl. Gen., 1: 561 (1982)) and an octopine synthetase polyadenylation signal (J. Gielen et al., EMBO J., 3: 835 (1984)).

The gene for use in the present invention can be obtained by cloning of cDNA or genomic DNA. Alternatively, if its sequence is already known, it can be obtained by chemical synthesis.

The vector of the present invention can be introduced into a plant cell indirectly via a plant-infecting virus or bacterium or directly by physical or chemical methods (I. Potrykus, Annu. Rev. Plant Physiol. Plant Mol. Bio. 42: 205 (1991)). For example, in the indirect introduction, infection with cauliflower mosaic virus, gemini virus, tobacco mosaic virus, bromo mosaic virus, A. tumefaciens, Agrobacterium rhizogenes or the like can be used. In the direct introduction, a microinjection method, an electroporation method, a polyethylene glycol method, a cell fusion method, a high-speed ballistic penetration method or the like can be applied.

According to the present invention, when the plant hormone signal transduction gene used as a selectable marker gene is introduced into a plant cell and expressed therein, the sensitivity for a plant hormone is changed, so that it causes physiological abnormal conditions in the cell in the presence of a plant hormone (regardless of endogenous or exogenous) and, as a result, puts the direction of the growth and differentiation of the cell out of order and causes abnormal behavior. Consequently, when a vector is constructed using the plant hormone signal transduction gene as a selectable marker gene together with a desired gene and the thus obtained vector is introduced into a plant cell, the selectable marker gene, namely a tissue solely formed from the cell into which the desired gene has been introduced, can be selected using abnormal behavior of the cell observed during the culturing as an index. It is not necessary to use a plant cell growth inhibitor which reduces plant cell activities for the selection.

Also, when this plant hormone signal transduction gene is used as a selectable marker gene, the gene product is not transferred from the transgenic cell into its peripheral non-transgenic cells and therefore does not exert its influence upon the peripheral cells. For example, when the CKI1 gene as a cytokinin signal transduction gene is introduced into a as a certain cell so that the sensitivity for cytokinin is improved, its influence does not reach its peripheral non-transgenic cells, and the cytokinin sensitivity of the peripheral cells is not improved. Consequently, since only the transgenic cell forms a multiple bud tissue due to the influence of the CKI1 gene, the tissue selected by culturing cells after the gene introduction process using the formation of the multiple bud tissue as an index is a tissue originated from a transgenic cell, namely a transgenic tissue. Thus, according to the present invention, selection efficiency of the transgenic tissue can be improved sharply.

Also, each of the plant hormone signal transduction gene and the plant hormone synthesis gene which is optionally used together with the plant hormone signal transduction gene, as a selectable marker gene of the present invention, is a gene inherently possessed by a plant or a gene naturally introduced into a plant through its infection with a bacterium or the like. Consequently, it can be considered that safety of the gene product upon the human body is fairly reliable.

Additionally, according to the present invention, such a selectable marker gene can be used by inserting it into such a position that it behaves integrally with the removable DNA element. When a gene is introduced into a plant using a vector having such a construction, the selectable marker gene loses its function by removal, together with the DNA element, at a certain probability from the DNA where they were once introduced and functioned, and, on the other hand, the desired gene which does not behave integrally with it remains on the same DNA and continues its function. Thus, in other words, a cell into which only the desired gene has been introduced can be obtained.

Moreover, disappearance of the function of this selectable marker gene can be detected as a behavioral change of the transgenic tissues under culturing similar to the case of the gene introduction, so that a tissue solely formed from the cell from which the function of selectable marker gene has been eliminated, in other words, a tissue solely formed from the cell into which only the desired gene has been introduced, can be selected certainly and easily at the stage of the cultured tissue. That is, in order to obtain a tissue solely formed from such a cell, the cell after a gene introduction treatment is firstly cultured and then transgenic tissue is selected and isolated using the abnormal behavior as an index, which is caused by the expression of the plant hormone signal transduction gene as a selectable marker gene. Since a tissue showing normal behavior of the original tissue is generated from the tissue having abnormal behavior during culturing of the isolated tissue, such a tissue can also be selected.

The vector of the present invention uses a plant hormone signal transduction gene, or the plant hormone signal transduction gene and a plant hormone synthesis gene, as a selectable marker gene(s) Consequently, when a desired gene is introduced into a plant using this vector, a tissue into which the desired gene has been introduced can be selected at a high efficiency using abnormal behavior of the plant cell as an index which is induced by the effect of the selectable marker gene, without using a plant cell growth inhibitor which reduces plant cell activities. Particularly, when the CKI1 gene is used as the plant hormone signal transduction gene, the plant cell into which this gene has been introduced is differentiated into a tissue having a characteristic morphology which can be easily distinguished with the naked eye. Furthermore, the resulting tissue can grow in a plant hormone-free medium, so that it is markedly convenient to select and culture the transgenic tissue.

Also, the plant hormone signal transduction gene and plant hormone synthesis gene are genes inherently possessed by plants or genes naturally introduced into plants through their infection with a bacterium or the like, so that it is fairly reliable in safety of the transgenic plants upon the human body when they are used as food even if the genes are expressed in the plant cell.

Additionally, when a removable DNA element is included in the construction of this vector and the selectable marker gene is inserted into such a position that it behaves integrally with the removable DNA element, the selectable marker gene loses its function by removal, together with the DNA element, at a certain probability from the DNA where they were once introduced and functioned after the gene introduction into a plant cell, and, on the other hand, the simultaneously introduced desired gene which is present in such a position that it does not behave integrally remains alone on the same DNA in an expression-possible manner. Accordingly, when such a construction is employed, this vector can be used repeatedly with no limitation for carrying out multiple introduction of genes into a single plant, by simply changing a part related to each desired gene to be introduced and not changing other constructions, such as the selectable marker gene and the like.

Also, in this case, disappearance of the function of the selectable marker gene can be detected as a behavioral change of the transgenic tissue similar to the case of the gene introduction, so that a tissue solely formed from the cell in which only the desired gene remains on the chromosome and keeps its function can be selected securely and easily at the stage of cultured tissues. Consequently, not only multiple introduction of genes can be carried out efficiently but also a transgenic individual solely formed from such a cell, namely a plant individual from which influences of the selectable marker gene are removed and possible dangers caused by the gene product are completely excluded, can be obtained without requiring a crossing step.

The present invention will be explained below based on Examples; however, it should not be construed as being limited thereto. Unless otherwise indicated, detailed experimental procedures in the following examples were carried out in accordance with the methods described in *Molecular Cloning*, 2 nd Edition (Sambrook et al. eds., Cold Spring Harbor Laboratory.Press, New York, 1989) or with respective manufacturers' manuals.

EXAMPLE 1

I. Construction of Plasmid pIPTPCKI-4

The GUS gene was digested from plasmid pB1221 (purchased from TOYOBO CO., LTD.) by restriction enzymes SacI and EcoRI, the digested ends were blunt-ended with T4 polymerase and then the resulting fragment was inserted into the HincII restriction enzyme site of plasmid pHSG398 (purchased from TAKARA SHUZO CO., LTD.) to obtain a plasmid pNOST.

Separately, the ipt gene promoter was amplified by PCR using plasmid pIPT2 having the ipt gene of a pathogenic *A. tumefaciens* strain P022 (International Publication No. WO 96/15252 and U.S. Pat. No. 5,965,791) as the template (as primers, 5'-AGCGGATAACAATTTCAC ACAGGAAAC-3' and 5'-AGTTTTTTGCGGTATCTTGAATACA A-3'were used in combination). The ipt gene promoter was inserted into the SmaI restriction enzyme site of plasmid pUC18 (purchased from TAKARA SHUZO CO., LTD.) to obtain a plasmid pIPT/Ap, and the ipt gene promoter thus inserted into pIPT/Ap was digested with restriction enzymes EcoRI and HindIII and inserted between the EcoRI-HindIII restriction enzyme sites of the pHSG398 to obtain a plasmid pIPTP/Cm.

Next, the ipt gene was again cleaved from the thus obtained pIPTP/Cm by digesting it with restriction enzymes KpnI and SaiII and inserted between the KpnI-XhoI restriction enzyme sites of plasmid pCKI16R1-2 (obtained from Dr. Kakimoto of Graduate School/Faculty of Science, Osaka University) to obtain a plasmid pIPTPCKI-1, and the ipt gene and the CKI1 structural gene connected thereto were digested from the thus obtained plasmid with restriction enzymes KpnI and SpeI and inserted between the KpnI-XbaI restriction enzyme sites of plasmid pNOST to obtain a plasmid pIPTPCKI-2.

The objective plasmid was obtained by digesting the CKI1 structural gene in which the ipt gene promoter and the nopaline synthetase polyadenylation signal were connected to each other, from the pIPTPCKI-2 with restriction enzymes KpnI and SseI, and then inserting the structural gene between the KpnI-SseI restriction enzyme sites of plasmid pIPT20 (Japanese Patent Application No. 10-202335) in such a manner that the rbcS prompter and the ipt gene connected thereto were replaced thereby, and the thus obtained plasmid was named plasmid pIPTPCKI-4.

Also, the plasmid pIPTPCKI-4 was introduced into Escherichia coli strain JM109, and the resulting strain was applied to international deposition as *E. coli* JM109 (pIPTPCKI-4) (National Institute, of Bioscience and Human-Technology, Agency of Industrial Science and Technology, the Ministry of International Trade and Industry (1-3, Higashi 1 chome, Tsukuba-shi, Ibaraki, Japan), international accession number FERM BP-6952, original deposition under Budapest Treaty on Dec. 15, 1999).

Figure 6:
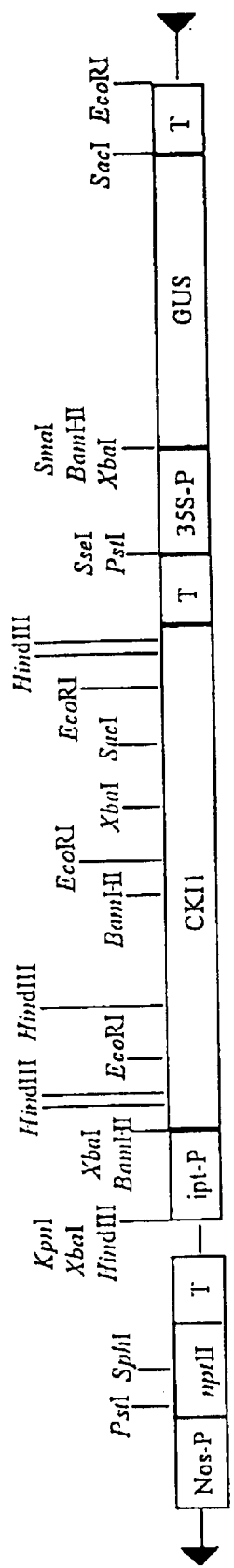
FIG. 6 is the restriction enzyme map of a T-DNA region in the structure of pIPTPCKI-4.

The construction scheme of pIPTPCKI-4 is shown in FIGS. 1 to 5, and the restriction enzyme map of a pIPTPCKI-4 region (T-DNA region) to be integrated into a plant chromosome is shown in FIG. 6. In FIG. 6, NOS-P indicates a nopaline synthetase promoter, T indicates a nopaline synthetase polyadenylation signal, ipt-P indicates the ipt gene promoter, 35S-P indicates a cauliflower mosaic virus 35S promoter, GUS indicates a β-glucuronidase gene and the small black triangles each indicates RB site and LB site dividing the T-DNA region.

As apparent from FIG. 6, this plasmid contains a plant hormone signal transduction gene, the CKI1 gene, as a selectable marker gene, and the NPTII gene and the GUS gene as models of the desired gene in the region to be integrated into a plant chromosome. Both of the NPTII gene which contributes to kanamycin resistance as described above and the GUS gene that produces a blue pigment in a cell containing the gene by metabolizing a specific substrate are genes generally used in the analysis of gene expression in plants.

II. Introduction of pIPTPCKI-4 into Agrobacterium

*A. tumefaciens* strain EHA 105 was inoculated into 10 ml of YEB liquid culture medium (beef extract 5 g/l, yeast extract 1 g/l, peptone 1 g/l, sucrose 5 g/l, 2 mM $MgSO_4$, pH 7.2 at 22° C. (unless otherwise noted, pH values at 22° C. are used hereinafter)) and cultured at 28° C. until $OD_{630}$ of the culture medium reached a value between 0.4 and 0.6. The resulting culture broth was centrifuged at 6,900×g and at 4° C. for 10 minutes, the thus collected cells were suspended in 20 ml of a buffer (10% glycerol, 1 mM HEPES, pH 7.0) and again centrifuged at 6,900×g and at 4° C. for 10 minutes, and then the resulting cells were suspended in 200 µl of YEB liquid medium and used as a cell suspension for plasmid introduction.

Introduction of pIPTPCKI-4 into Agrobacterium was carried out by electroporation. That is, an electric pulse of 2.5 kV, 25 µF and Ω was added at an inter-electrode distance of 0.2 cm to 50 µl of the cell suspension for plasmid introduction prepared in the above step I by mixing 3 µg of pIPTPCKI-4 to introduce pIPTPCKI-4 into Agrobacterium (GENE PULSER II manufactured by Bio-Rad). The cells after electroporation were suspended in 200 µl of YEB liquid medium and cultured at 25° C. for 1 hour on a shaker, and the resulting cells were spread on YEB agar medium (agar 1.5 w/v %) supplemented with 50 mg/l of kanamycin and cultured at 28° C. for 2 days to select a pIPTPCKI-4-introduced strain. Introduction of the pIPTPCKI-4 was finally confirmed by digesting a plasmid which had been extracted from the selected strain by the alkali method with restriction enzymes and then comparing electrophoresis patterns of the digested fragments. III. Introduction of pIPTPCKI-4 from Agrobacterium into *Arabiopsis thaliana* and analysis of the transgenic *Arabiopsis thaliana*.

Calli of *Arabiopsis thaliana* prepared in accordance with a usual method (*Cell Engineering Supplement, Plant Engineering Series* 4, "Experimental Protocols of Model Plants—Rice and Arabidopsis thaliana", pp. 138-139) were infected with the pIPTPCKI-4-introduced *A. tumefaciens* obtained in the above step II. When the *Arabiopsis thaliana* calli after the infection treatment were bedded on a Murashige-Skoog (MS) medium (T. Murashige and F. Skoog, *Physiol. Plant.*, 15: 473 (1962); supplemented with 1 w/v % sucrose and 0.8 w/v % agar as other components) which had been further supplemented with 0.5 mg/l of indolebutyric acid, auxin, as a plant hormone, and 150 mg/l of cefotaxime as an antibiotic, and then cultured at 23° C. under 5,000 lux, differentiation of multiple buds was observed in 21 of the 40 tested calli. These buds were subjected to a GUS activity test in accordance with the method of Jefferson et al., and the GUS activity was detected from all of them.

Naturally, when buds are differentiated from *Arabiopsis thaliana* calli, it is necessary to supply the calli with cytokinin as a plant hormone from the outside. Accordingly, cytokinin is added to a medium for culturing these calli. However, in the present test, differentiation of multiple buds was observed in 50% or more of the calli cultured using the cytokinin-free medium. This result suggests that, since the CXI1 gene was introduced into the callus-constituting cells, cytokinin sensitivity of the cells was improved so that influence of the endogenous cytokinin inherently produced by the cells per se was very largely exerted upon the cells. Also, the activity of the GUS gene as the desired gene was detected without exception from all of the tissues thus selected using the multiple bud morphology as an index, which was formed by the action of the selectable marker gene, the CKI1 gene. That is, the selection efficiency of transgenic tissues was 100% in this test.

EXAMPLE 2

1. Construction of Plasmid pIPCK-1

The plasmid pIPTPCKI-2 obtained in Example 1 was digested once with a restriction enzyme SseI, the digested ends were blunt-ended with T4 polymerase and then a KpnI linker was inserted into the digested region to obtain a plasmid pIPTPCKI-3. The objective plasmid pIPCK-1 was obtained by digesting the CKI1 structural gene in which the ipt gene promoter and the nopaline synthetase polyadenylation signal were connected to each other, from the thus obtained pIPTPCKI-3 with a restriction enzyme KpnI, and then inserting the resulting fragment into the KpnI restriction enzyme site of the plasmid pIPT20.

Also, the plasmid pIPCK-1 was introduced into *Escherichia coli* strain JM109, and the resulting strain was applied to international deposition as *E. coli* JM109 (pIPCK-1) (National Institute of Bioscience and Human-Technology, Agency of Industrial Science and Technology, the Ministry of International Trade and Industry (1-3, Higashi 1 chome, Tsukuba-shi, Ibaraki, Japan), international accession number FERM BP-6951, original deposition under Budapest Treaty on Dec. 15, 1999).

Figure 7:
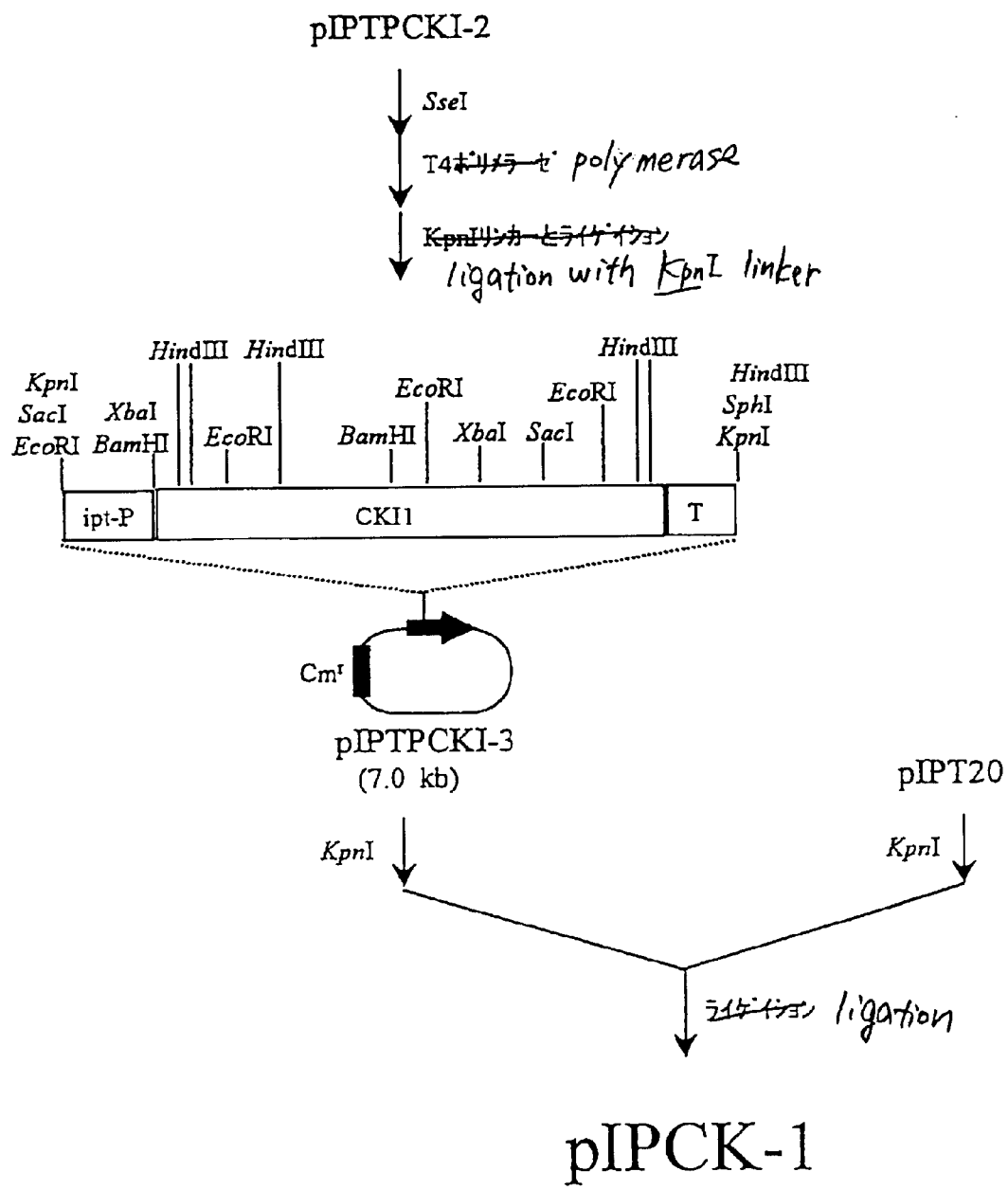
FIG. 7 is a view showing construction scheme of pIPCK-1.
Figure 8:
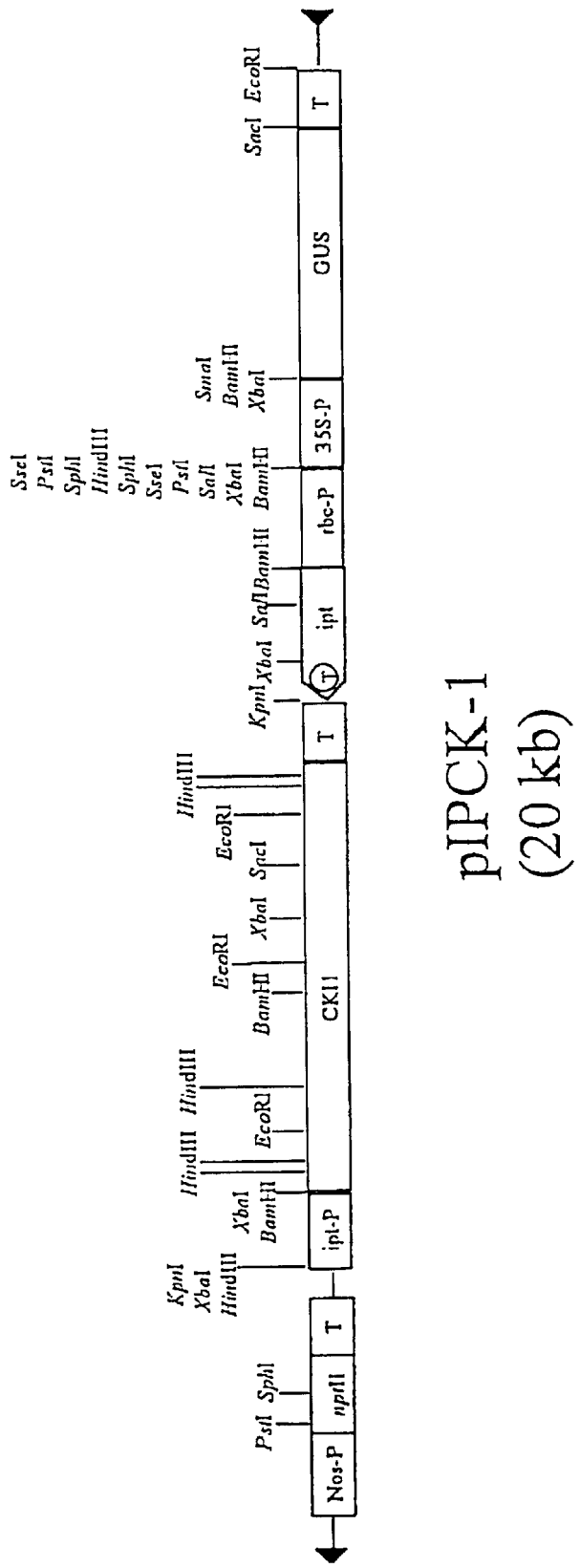
FIG. 8 is the restriction enzyme map of a T-DNA region in the structure of pIPCK-1.

The construction scheme of pIPCK-1 is shown in FIG. 7., and the region of pIPCK-1 to be integrated into a plant chromosome is shown in FIG. 8. In FIG. 8, the encircled T means a polyadenylation signal of the ipt gene per se and rbc-P means the rbcS gene promoter. Other symbols are the same as those used in FIG. 6.

As apparent from FIG. 8, this plasmid contains a plant hormone signal transduction gene, the CKI1 gene, and a plant hormone synthesis gene, the ipt gene, as selectable marker genes in the region to be integrated into a plant chromosome.

II. Introduction of pIPCK-1 into *Arabiopsis thaliana*

In the same manner as described in the steps II and III of Example 1, *Arabiopsis thaliana* calli were infected with the plasmid pIPCK-1-introduced *A. tumefaciens* strain ERA 105, and the calli were cultured. As a result, differentiation of multiple buds more compact than the case of the introduction of pIPTPCKI-4 was observed in 17 of the 40 tested calli on the 20 th day after the *A. tmefaciens* infection. These buds were subjected to the GUS activity test, and the GUS activity was detected from all of them.

Also, the buds differentiated from pIPCK-1-introduced calli showed a morphology which was slightly different from that observed in. Example 1. This result suggests that certain influences were exerted by the improvement of cytokinin sensitivity due to the action of the CKI1 gene in the pIPCK-1-introduced cells and by the supply of cytokinin produced by the action of the ipt transgenic together with the CKI1 gene, in addition to the endogenous cytokinin inherently produced by the cells.

COMPARATIVE EXAMPLE 1

A vector plasmid pBI121 for introducing a gene into a plant (purchased from TOYOBO CO., LTD.) was introduced into *Arabiopsis thaliana* calli in the same manner as described in the steps II and III of Example 1, and the calli were cultured, but differentiation of buds was not observed from the 30 tested calli even after 20 days of the *A. tumefaciens* infection. Also, when the plasmid pBI121 is simply introduced into plant cells like the case of this comparative example, only the NPTII gene and GUS gene are integrated into the plant chromosome.

COMPARATIVE EXAMPLE 2

Figure 9:
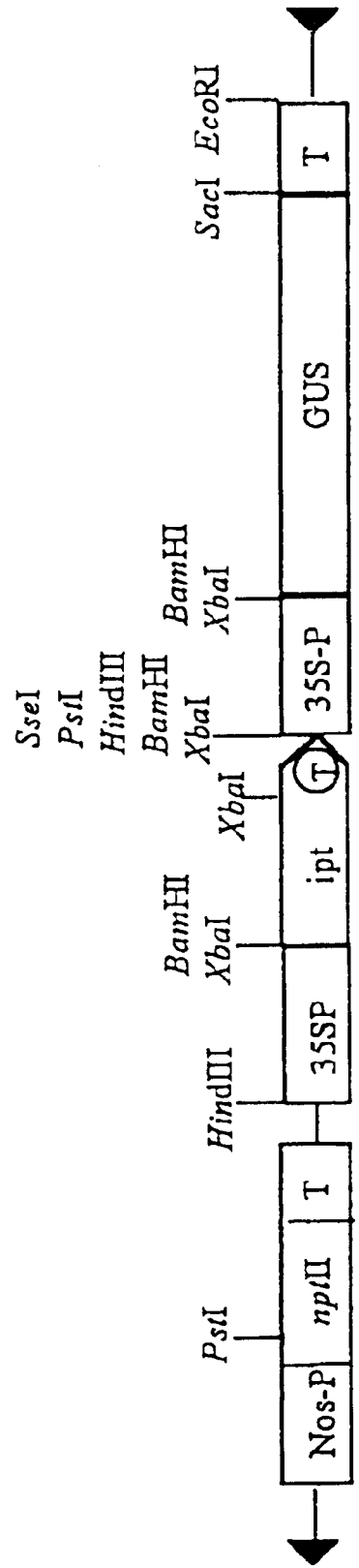
FIG. 9 is the restriction enzyme map of a T-DNA region in the structure of pIPT5.

A plasmid pIPT5 containing the GUS gene as a model of the desired gene and the ipt structural gene under control of CaMV35S promoter as a selectable marker gene (FIG. 9) was introduced into *Arabidopsis thaliana* calli in the same manner as described in the steps II and III of Example 1, and the calli were cultured. As a result, differentiation of buds with destroyed apical dominance, probably, due to the influence of the ipt gene was observed in 7 of the 40 tested calli. However, only one of the buds showed the GUS activity at the GUS activity test.

COMPARATIVE EXAMPLE 3

Figure 10:
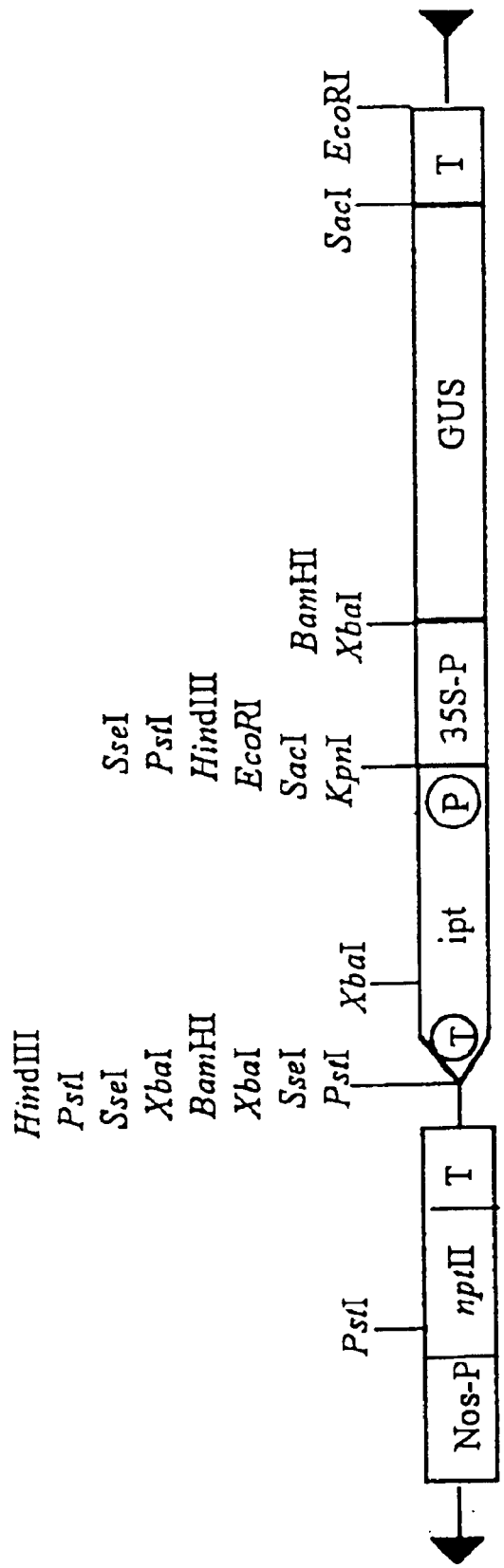
FIG. 10 is the restriction enzyme map of a T-DNA region in the structure of PIPT10.
Figure 11:
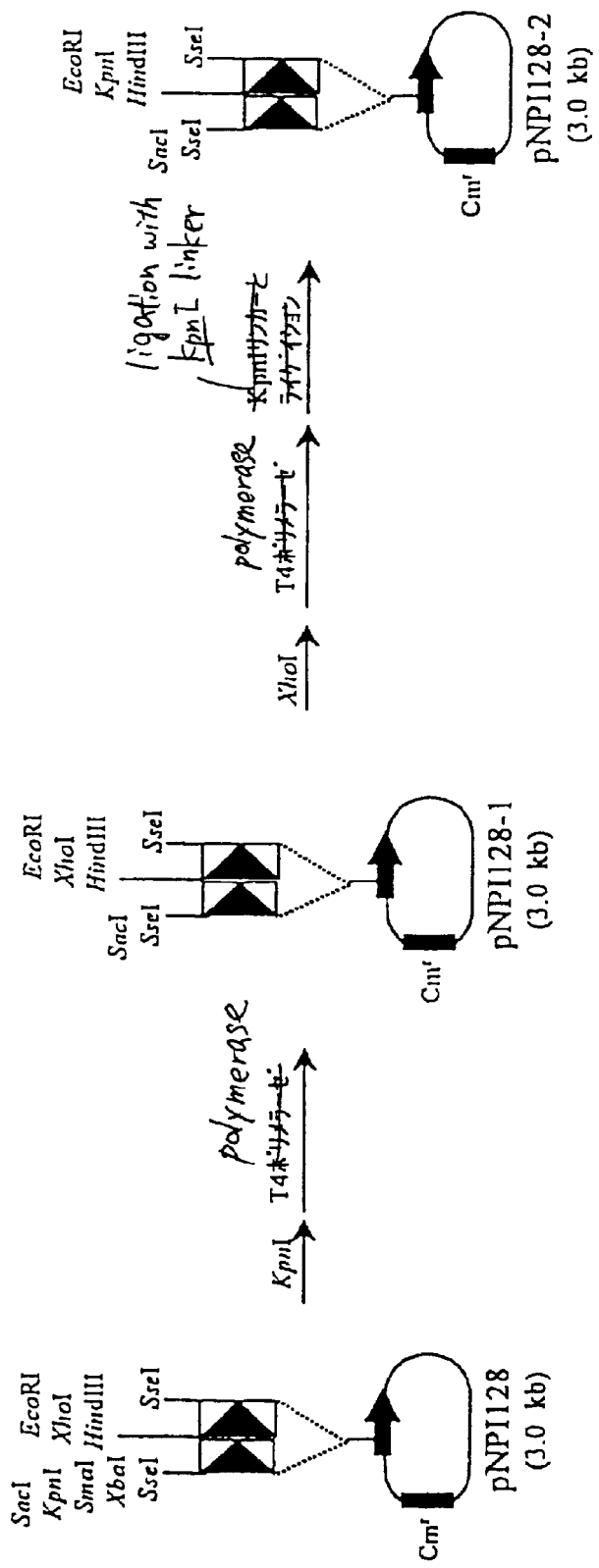
FIG. 11 is a diagram of the construction of pNPI128-2 in the pMATCK-1 construction scheme.
Figure 12:
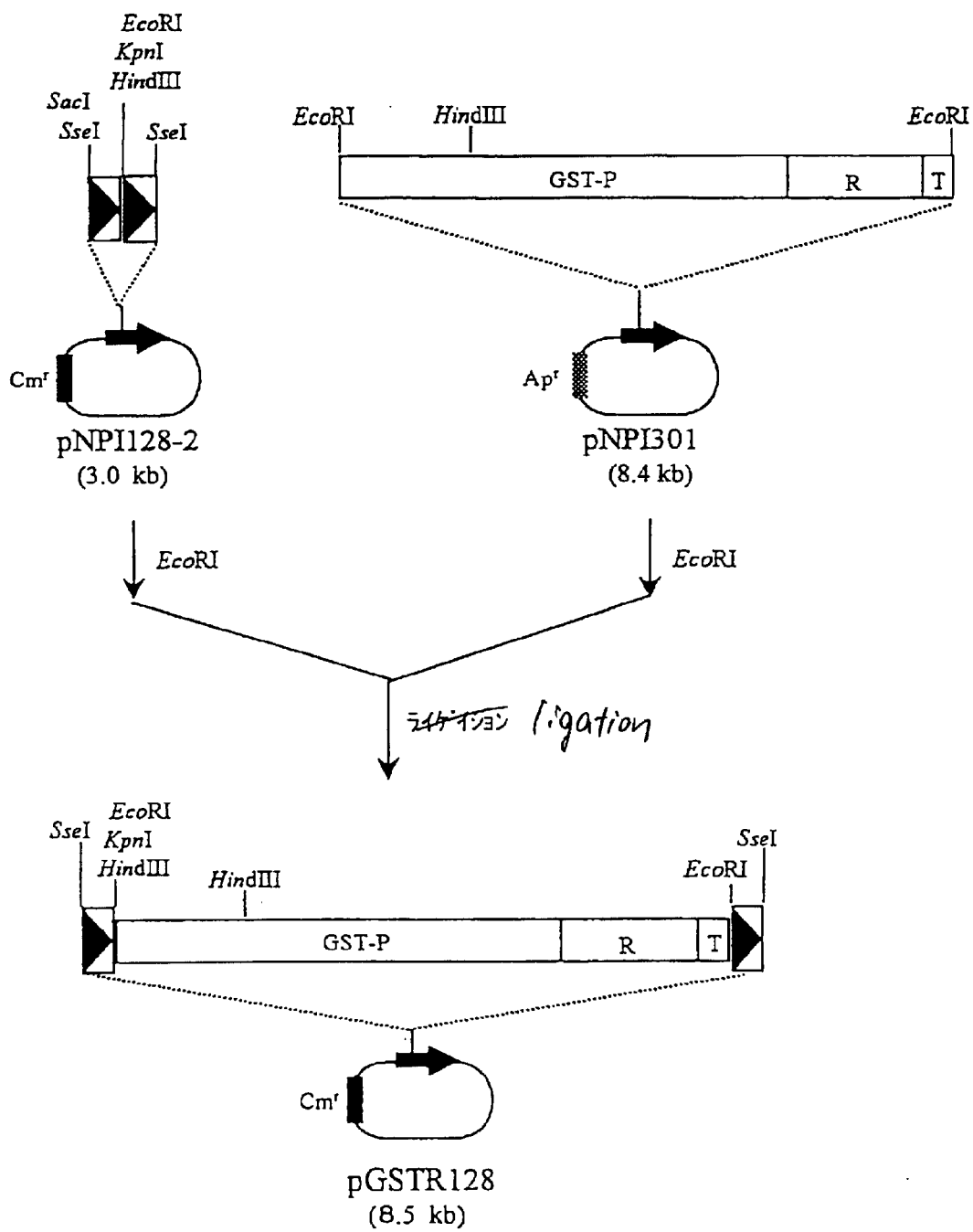
FIG. 12 is a diagram of the construction of pGSTR128 from pNPI128-2 in the pMATCK-1 construction scheme.
Figure 13:
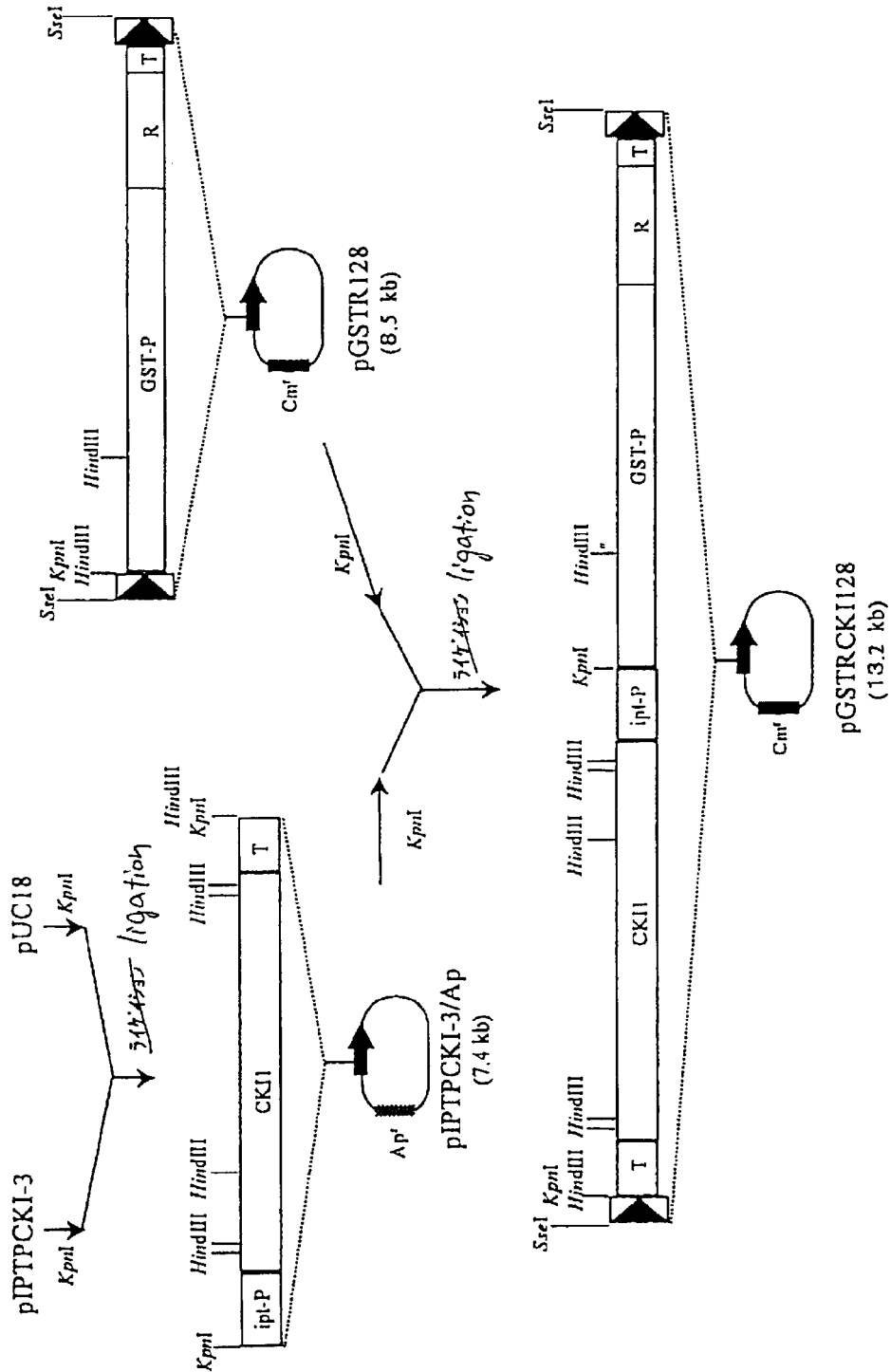
FIG. 13 is a diagram of the construction of pGSTRCKI128 from pIPTPCKI-3 and pGSTR128 in the pMATCK-1construction scheme.

A plasmid pIPT10 containing the GUS gene as a model of the desired gene and the ipt structural gene under control of its inherent promoter as a selectable marker gene (FIG. 10), was introduced into *Arabidopsis thaliana* calli in the same manner as described in the steps II and III of Example 1, and the calli were cultured. As a result, differentiation of buds with destroyed apical dominance was observed similar to the case of Comparative Example 2 in 2 of the 40 tested calli. However, none of the buds showed the GUS activity at the GUS activity test.

EXAMPLE 3

I. Construction of Plasmid pMATCK-1

In order to delete the SmaI and XbaI restriction enzyme sites from the plasmid pNPI128 (International Publication No. WO 96/15252 and U.S. Pat. No. 5,965,791), this plasmid was once digested with a restriction enzyme KpnI, termini of the thus obtained fragments were blunt-ended with T4 polymerase and then they were ligated again. Next, the thus obtained plasmid pNPI128-1 was digested with a restriction enzyme XhoI, and the resulting fragment was blunt-ended with T4 polymerase and then a KpnI linker was inserted into the digested site to obtain a plasmid pNPI128-2. An R -structural gene in which the GST-II gene promoter and the nopaline synthase polyadenylation signal were connected to each other was digested from the plasmid pNPI301 (JP-A-10-327860) with a restriction enzyme EcoRI and inserted into the EcoRI restriction enzyme site of the plasmid pNPI128-2 to obtain a plasmid pGSTR128. Also, the R structural gene used herein is a gene which encodes a recombinant enzyme separated from a yeast site-specific recombination system.

On the other hand, the CKI1 structural gene in which the ipt gene promoter and the nopaline synthase polyadenylation signal were connected to each other was digested from the plasmid pIPTPCKI-3 obtained in the step I of Example 2 with a restriction enzyme KpnI and inserted into the KpnI restriction enzyme site of the plasmid pUC18 (purchased from TAKARA SHUZO CO., LTD.) to obtain a plasmid pIPTPCKI-3/Ap. Next, the ipt gene promoter, the CKI1 structural gene and the nopaline synthase polyadenylation signal were again digested from the plasmid pIPTPCKI-3/Ap with a restriction enzyme KpnI and inserted into the KpnI restriction enzyme site of the plasmid pGSTR128 to obtain a plasmid pGSTRCKI128.

The objective plasmid was obtained by digesting a region sandwiched by the recombinant sequence Rs's of the yeast site-specific recombinant system from the plasmid pGSTRCKI128 with a restriction enzyme SseI and inserting the resulting region into the SseI restriction enzyme site of the plasmid pBI121, and the thus obtained plasmid was named pMATCK-1.

Also, the plasmid pMATCK-1 was introduced into Escherichia coli strain JM109, and the resulting strain was applied to international deposition as *E. coli* JM109 (pMATCK-1) (National Institute of Bioscience and Human-Technology, Agency of Industrial Science and Technology, the Ministry of International Trade and Industry (1-3, Higashi 1 chome, Tsukuba-shi, Ibaraki, Japan), international accession number FERM BP-6953, original deposition under Budapest Treaty on Dec. 15, 1999.

Figure 14:
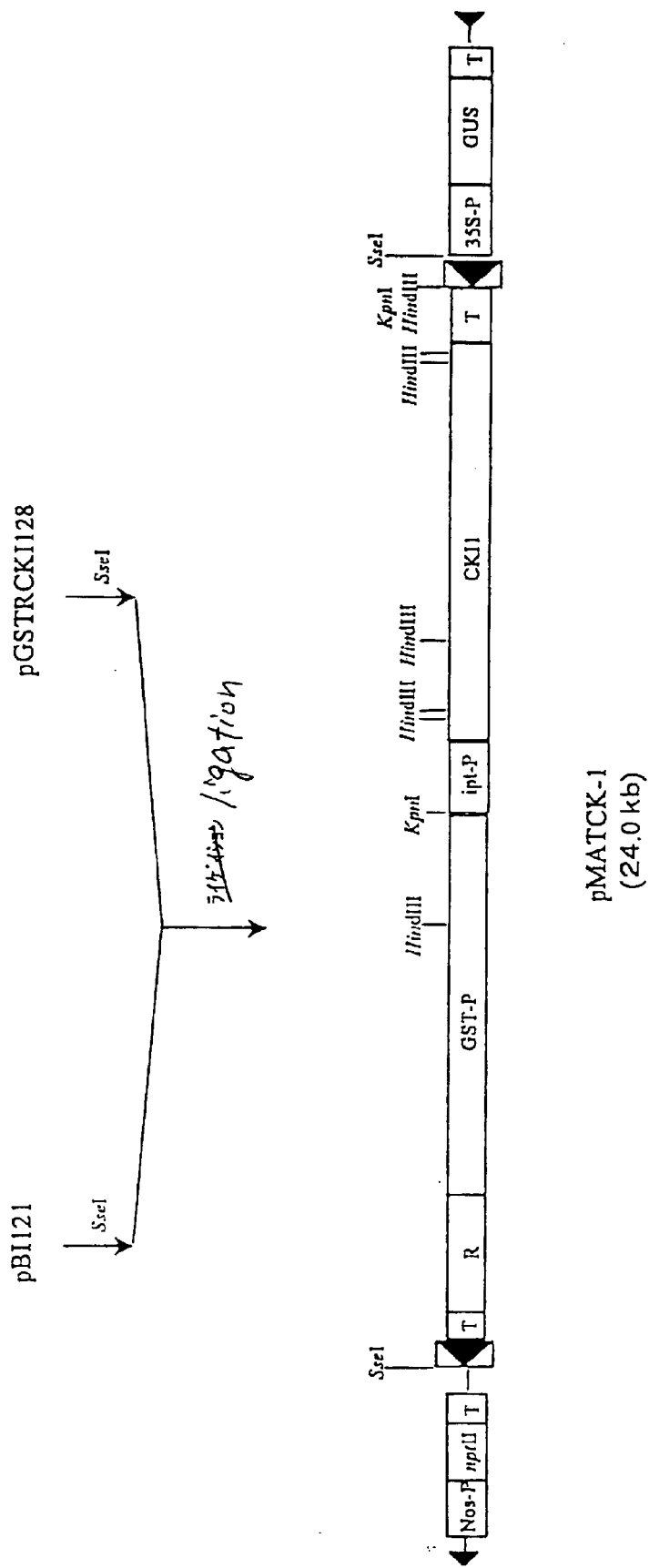
FIG. 14 is a diagram of the construction of pMATCK-1 from pGSTRCKI128 in the pMATCK-1 construction scheme, and the structure of the thus constructed pMATCK-1.
Figure 15:
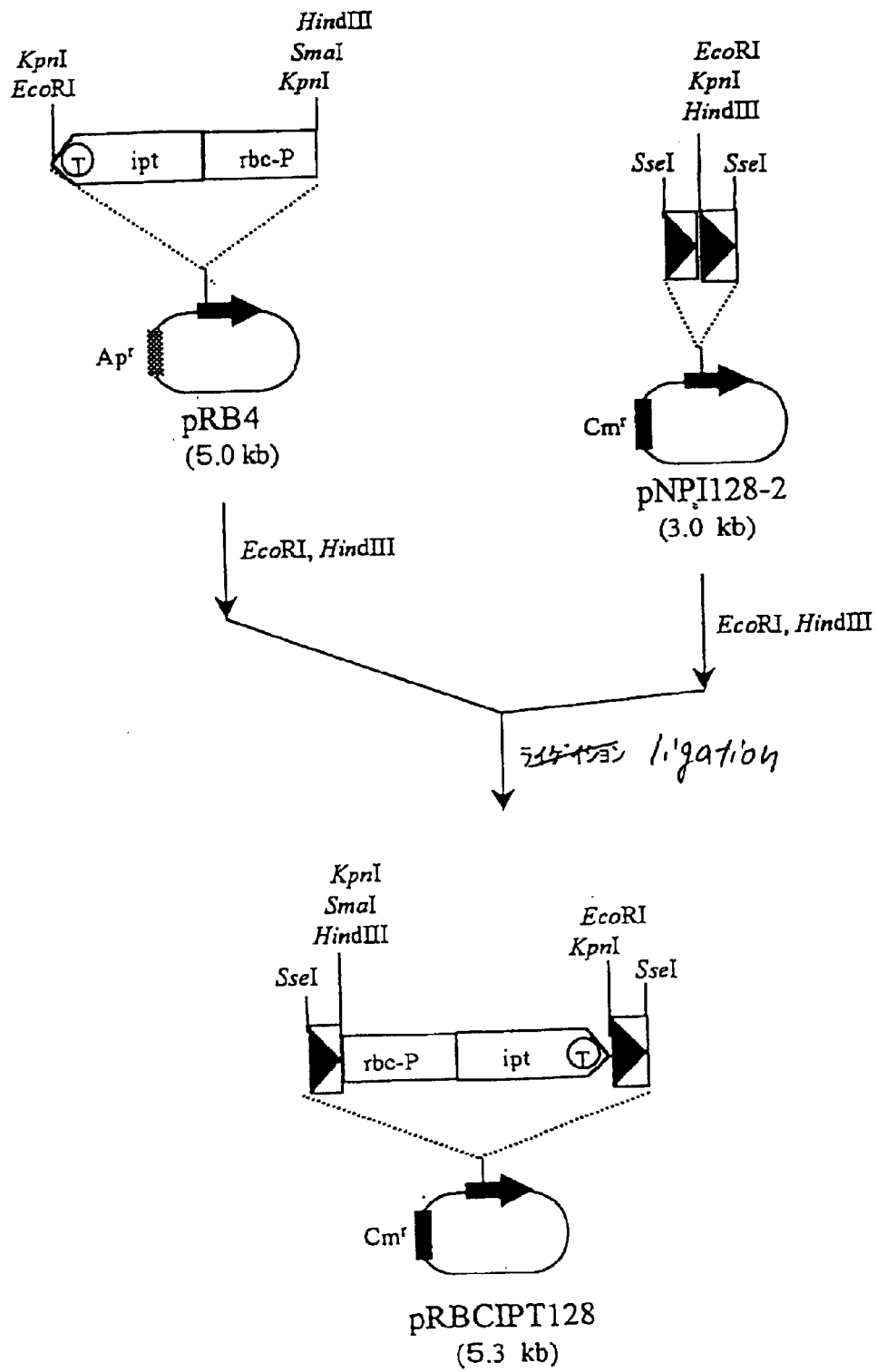
FIG. 15 is a diagram of the construction of pRBCIPT128 in the pMATIPCK-1 construction scheme.
Figure 16:
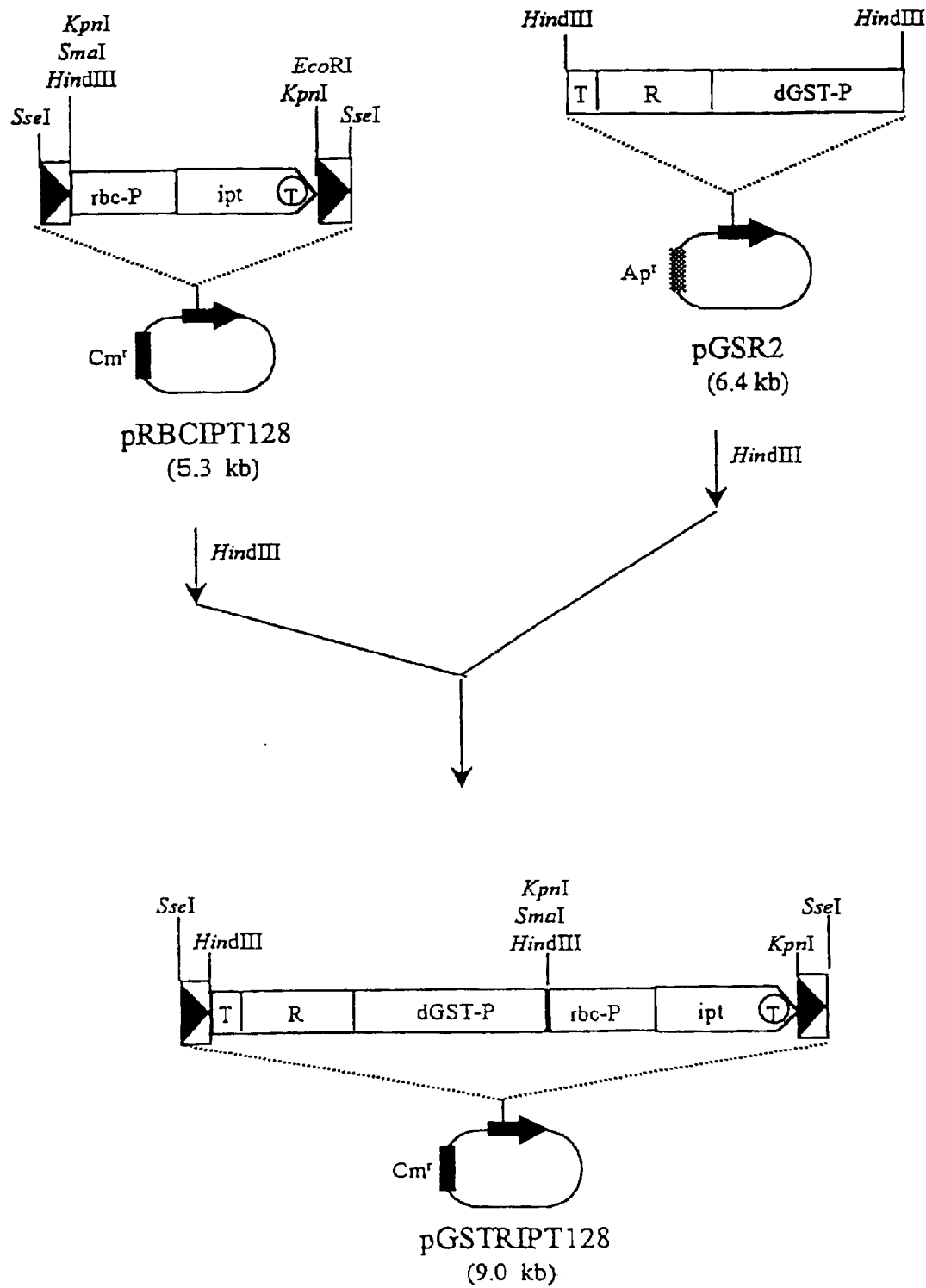
FIG. 16 is a diagram of the construction of pGSTRIPT128 from pRBCIPT128 in the pMATIPCK-1 construction scheme.
Figure 17:
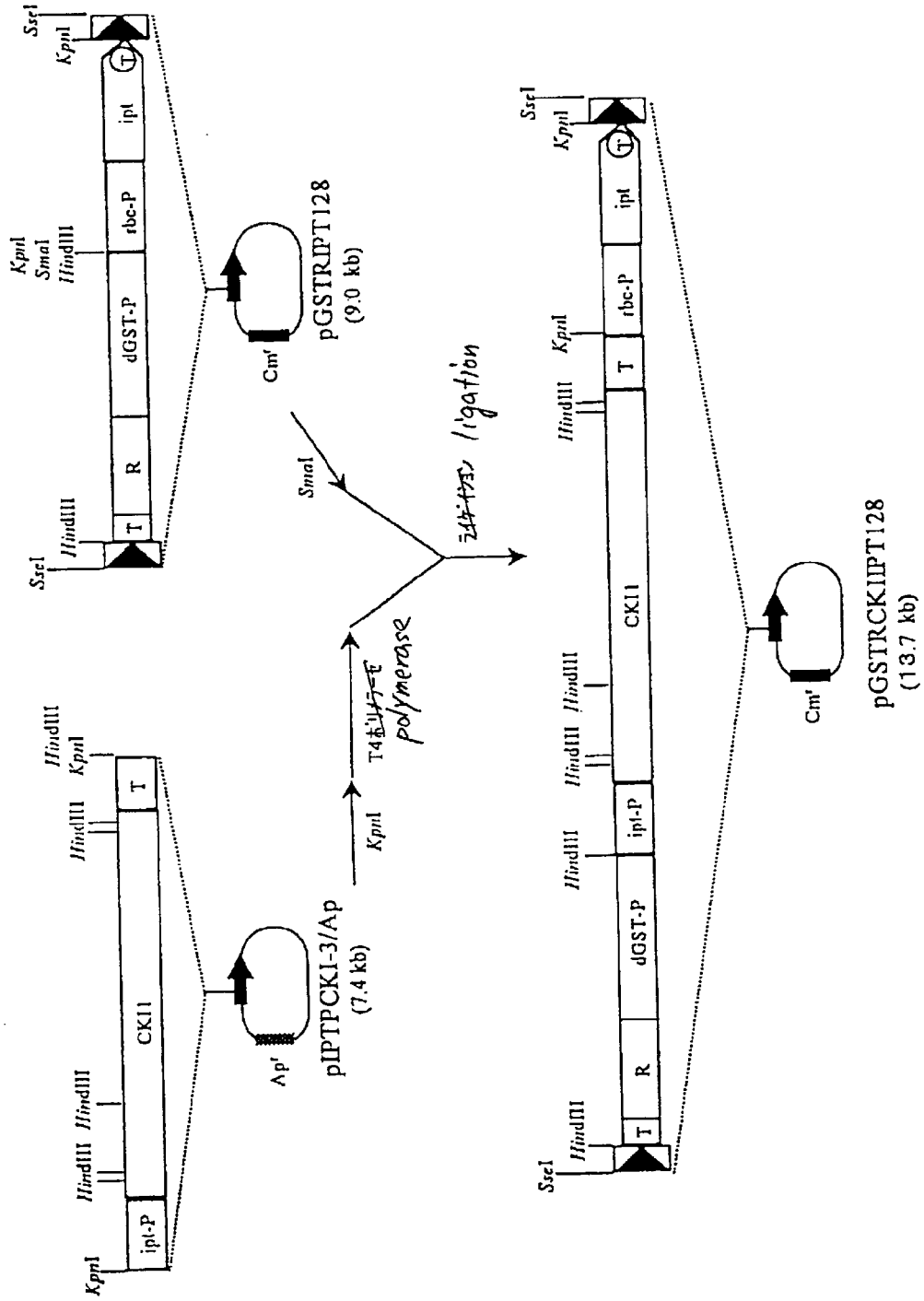
FIG. 17 is a diagram of the construction of pGSTRCKI-IPT128 from pIPTPCKI-3/Ap and pGSTRIPT128 in the pMATIPCK-1 construction scheme.

The construction scheme of pMATCK-1 is shown in FIGS. 11 to 14, and the restriction enzyme map of a region of the pMATCK-1 to be integrated into a plant chromosome. (T-DNA region) is shown in FIG. 14. In FIG. 14, GST-P indicates the promoter of the GST-II gene, the triangles of arrowhead shape indicate the recombinant Rs and their sequential directions and other symbols are the same as those used in FIG. 6.

As apparent from FIG. 14, this plasmid pMATCK-1 is the same as the plasmid pIPTPCKI-4 constructed in the step I of Example 1 in terms that it contains a plant hormone signal transduction gene, the CKI1 gene, as a selectable marker gene, and the NPTII gene and the GUS gene as models of the desired gene, in the region to be integrated into a plant chromosome, but is different therefrom in terms that it contains the recombinant enzyme gene (R gene) and recombinant sequences of a yeast site-specific recombinant system, and the CKI1 gene used as a selectable marker gene is present in a region sandwiched by the recombinant sequences. Accordingly, when a gene is introduced into a plant using, this vector, as a result of expression of a recombinant enzyme, the selectable marker gene once integrated into the plant chromosome is removed together with the recombinant enzyme and recombinant sequences, and, on the other hand, the desired gene remains as such on the chromosome and continues to exert its functions.

II. Introduction of pMATCK-1 into *Arabiopsis thaliana* and Analysis of the Transgenic *Arabiopsis thaliana*

In the same manner as described in the steps II and III of Example 1, 1*Arabiopsis thaliana* calli were infected with the plasmid pMATCK-1-introduced

*A. tumefaciens* strain EHA 105, and the calli were cultured. As a result, differentiation of multiple buds similar to the case of the introduction of pIPTPCKI-4 was observed in all of the 30 tested calli on the 20 th day after the *A. tumefaciens* infection. Among these buds, 17 buds differentiated from different calli were subjected to the GUS activity test, and the GUS activity was detected in all of them.

Also, chromosomal DNA was extracted by the CTAB method from each of the 17 buds having the GUS activity and subjected to PCR using two primers which had been designed in such a manner that they were able to bind to the NPTII gene and the GUS gene, respectively. The thus amplified DNA fragments were analyzed by electrophoresis, and disappearance of the CKI1 gene and R gene was detected in two of these buds (PCR and electrophoresis were carried out in accordance with the conditions described in International Publication No. WO 96/15252 and U.S. Pat. No 5,965,791). This result suggests that the activity of the GST-II gene promoter used as the R gene promoter was induced by a physiological change in the cells caused by a hindrance added to the plant tissues when this test was carried out, and as a result, the R gene was expressed to cause removal of the region sandwiched by the recombinant sequence Rs's of the site-specific recombination system. Also, in these two buds, an excision event of the morphological abnormality-inducing CKI1 gene from the chromosome was detected, but no significant difference in morphology was detected in comparison with the simultaneously analyzed other 15 buds in which the CKI1 gene was kept on the chromosome. This result suggests that the culturing period of 20days after infection with *A. tumefaciens* was so short that they did not reach a stage at which a difference in morphology detectable with the naked eye could be detected between both cases.

EXAMPLE 4

I. Construction of pMATIPCK-1

The rbcS promoter and the ipt gene connected thereto were digested from the plasmid pRB4 (Japanese Patent Application No. 10-202335) with restriction enzymes EcoRI and HindIII and inserted between the EcoRi-HindIII restriction enzyme sites of the plasmid pNPI128-2 obtained in the step I of Example 3 to obtain a plasmid pRBCIPT128. An R structural gene in which the GST-II gene promoter and the nopaline synthase polyadenylation signal were connected to each other was digested from the plasmid pGSR2 (Japanese Patent Application No. 10-202335) with a restriction enzyme HindIII and inserted into the HindIII restriction enzyme site of the plasmid pRBCIPT128 to obtain a plasmid pGSTRIPT128.

On the other hand, the CKI1 structural gene in which the ipt gene promoter and the nopaline synthase polyadenylation signal were connected to each other was digested from the plasmid pIPTPCKI-3/Ap obtained in the step I of Example 2 with a restriction enzyme KpnI. The thus digested fragment was blunt-ended with T4 polymerase and inserted into the SmaI restriction enzyme site of the plasmid pGSTRIPT128 to obtain a plasmid pGSTRCKIIPT128.

The objective plasmid was obtained by digesting a region sandwiched by the recombinant sequence Rs's of the yeast site-specific recombinant system from the plasmid pGSTRCKIIPT128 with a restriction enzyme SseI and inserting the resulting region into the SseI restriction enzyme site of the plasmid pBI121, and the thus obtained plasmid was named pMATIPCK-1.

Also, the plasmid pMATIPCK-1 was introduced into *Escherichia coli* strain JM109, and the resulting strain was applied to international deposition as *E. coli* JM1O9 (pMATIPCK-1) (National Institute of Bioscience and Human-Technology, Agency of Industrial Science and Technology, the Ministry of International Trade and Industry (1-3, Higashi 1 chome, Tsukuba-shi, Ibaraki, Japan), international accession number FERM BP-6954, original deposition under Budapest Treaty on Dec. 15, 1999)

Figure 18:
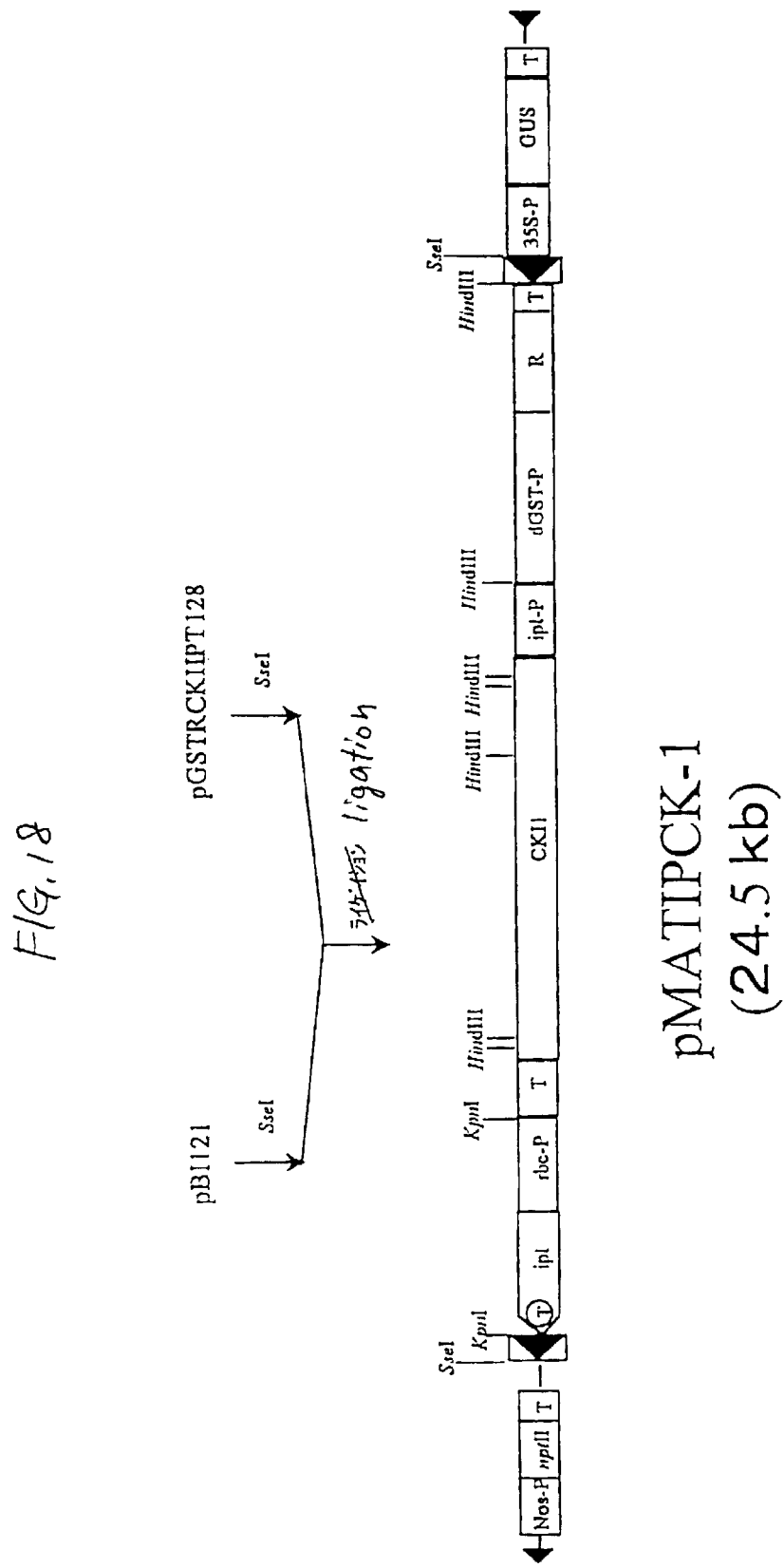
FIG. 18 is a diagram of the construction of pMATIPCK-1 from pGSTRCKIIPT128 to in the pMATIPCK-1 construction scheme, and the structure of the thus constructed pMATIPCK-1.

The construction scheme of pMATIPCK-1 is shown in FIGS. 15 to 18, and the restriction enzyme map of a region of the pMATIPCK-1 to be integrated into a plant chromosome (T-DNA region) is shown in FIG. 18. The symbols shown in FIG. 18 are the same as those defined in FIGS. 6, 8 and 14.

As apparent from FIG. 18, this plasmid pMATIPCK-1is the same as the plasmid pIPCK-1 constructed in the step. I of Example 2 in terms that it contains a plant hormone signal transduction gene, the CKI1 gene, and a plant hormone synthesis gene, the ipt gene, as selectable marker genes, and the NPTII gene and the GUS gene as models of the desired gene, in the region to be integrated into a plant chromosome, but is different therefrom in terms that it contains the recombinant enzyme gene (R gene) and recombinant sequences of a yeast site-specific recombinant system, and the CKI1 gene and the ipt gene used as selectable marker genes are present in a region sandwiched by the recombinant sequences. Consequently, the selectable marker genes in this vector show the same behavior as the case of the plasmid pMATCK-1 constructed in the step I of Example 3.

II. Introduction of pMATIPCK-1 into *Arabidopsis thaliana* and Analysis of the Transgenic *Arabidopsis thaliana*.

In the same manner as described in the steps II and III of Example 1, *Arabiopsis thaliana* calli were infected with the plasmid pMATIPCK-1-introduced *A. tumefaciens* strain ERA 105, and the calli were cultured. As a result, differentiation of multiple buds more compact in comparison with the case of the introduction of pIPTPCKI-4 was observed in all of the 30 tested calli on the 20 th day after the *A. tumefaciens* infection. Among these, 7 buds differentiated from different calli were subjected to the GUS activity test, and the GUS activity was detected in all of them.

While the invention has been described in detail and with reference to specific examples thereof, it will be apparent to one skilled in the art that various changes and modifications can be made therein without departing from the spirit and scope thereof.

The priority applications, Japanese patent application Nos. Hei 11-828, filed Jan. 6, 1999, and Hei. 11343037 filed Dec. 2, 1999, are incorporated herein by reference in their entirety.

What is claimed is:

1. A vector for introducing a gene into a plant, which comprises:

a desired gene, a cytokinin signal transduction gene which comprises the CKI1 gene from *Arabidopsis thaliana* and a cytokinin synthesis gene together as selectable marker genes, and a removable DNA element, wherein the selectable marker genes are positioned such that they behave integrally with the removable DNA element, and wherein the desired gene is positioned such that it does not behave integrally with the removable DNA element.

2. The vector according to claim 1, wherein the selectable maker genes are present within the removable DNA element.

3. The vector according to claim 1, wherein the cytokinin synthesis gene is the isopentenyl transferase (ipt) gene which is present on the T-DNA of *Agrobacterium tumefaciens*.

4. The vector according to claim 1, wherein the removable DNA element is derived from a site-specific recombination system.

* * * * *